(12) United States Patent
Xiao et al.

(10) Patent No.: US 6,734,006 B2
(45) Date of Patent: May 11, 2004

(54) REGULATION OF HUMAN TRANSMEMBRANE SERINE PROTEASE

(75) Inventors: Yonghong Xiao, Cambridge, MA (US); Richard W. Gedrich, Guilford, CT (US)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/879,792

(22) Filed: Jun. 13, 2001

(65) Prior Publication Data

US 2002/0061850 A1 May 23, 2002

Related U.S. Application Data

(60) Provisional application No. 60/283,648, filed on Apr. 16, 2001, provisional application No. 60/283,353, filed on Apr. 13, 2001, and provisional application No. 60/211,224, filed on Jun. 13, 2000.

(51) Int. Cl.$^7$ ............................. C12N 9/50; C12N 1/20; C12N 15/74; C12Q 1/37; C12P 21/06
(52) U.S. Cl. ..................... 435/226; 435/23; 435/69.1; 435/325; 435/252.3; 435/320.1; 435/219; 536/23.2; 536/24.3; 536/24.31; 536/23.1
(58) Field of Search ................. 435/226, 69.1, 435/219, 325, 252.3, 320.1, 23; 536/23.2, 23.1, 24.3, 24.31

(56) References Cited

FOREIGN PATENT DOCUMENTS

| WO | WO 99/62942 | 12/1999 |
|---|---|---|
| WO | WO 99/64608 | 12/1999 |
| WO | WO 00/00605 | 1/2000 |
| WO | WO 01/36604 | 5/2001 |
| WO | WO 01/36645 | 5/2001 |

OTHER PUBLICATIONS

Van de Loo et al. , Proc. Natl. Acad. Sci. 92:6743–6747, 1995.*
Broun et al. , Science 282:1315–1317, 1998.*
Bork, Genome Research, 10:348–400, 2000.*
Dias Neto et al. , GenBank accession No. AW845106, May 19, 2000.*
Kim et al. , Biochim. Biophys. Acta 1518:204–209, Mar. 19, 2001.*
Kim et al., "Cloning and expression of novel mosaic serine proteases with and without a transmembrane domain from human lung," Biochim. Biophys. Acta 1518, 204–09, 2001.
GenBank Accession No. AK027798, submitted May 10, 2001.
GenBank Accession No. XM_052099, submitted Aug. 23, 2001.
GenBank Accession No. XM_052100, submitted Aug. 23, 2001.
GenBank Accession No. AB048796, submitted Sep. 12, 2000.
GenBank Accession No. AB048797, submitted Sep. 12, 2000.
Hillier L. et al., "yl73c10.r1 Soares placenta Nb2HP *Homo sapiens* cDNA clone IMAGE:144882 3' similar to SP:HEPS_RAT Q05511 Serine Protease Hepsin; contains MER22 repetitive element; mRNA sequence"; Database EM_EST Online! EMBL; Jun. 10, 1995.
Tanimoto H. et al, "Hepsin, a cell surface serine protease identified in hepatoma cells, is overexpressed in ovarian cancer", Cancer Research 57, Jul. 15, 1997, pp 2884–2887.
Hattori M. et al., "*Homo sapiens* genomic DNA, chromosome 11q clone:RP11–728F11, complete sequences", Database EM HUM Online! EMBL; Nov. 27, 1999.
Paoloni–Giacobino A. et al., "Cloning of the TMPRSS2 gene, which encodes a novel serine protease with transmembrane, LDLRA, and SRCR domains and maps to 21q22.3", Genomics, Sep. 15, 1997, pp 309–320, vol. 44, No. 3.
Hooper J.D. et al., "Type II transmembrane serine proteases" Journal of Biological Chemistry; Jan. 12, 2001; pp 857–860; vol. 276, No. 2.

* cited by examiner

*Primary Examiner*—Rebecca Prouty
*Assistant Examiner*—Delia Ramirez
(74) *Attorney, Agent, or Firm*—Banner & Witcoff, Ltd.

(57) ABSTRACT

Reagents that regulate human transmembrane serine protease activity and reagents that bind to human transmembrane serine protease gene products can be used to regulate extracellular matrix degradation. Such regulation is particularly useful for treating COPD, metastasis of malignant cells, tumor angiogenesis, inflammation, atherosclerosis, neurodegenerative diseases, and pathogenic infections.

23 Claims, 9 Drawing Sheets

FIG. 1

BLASTP - query = 147_TR1; Hit = swiss|O15393|TMS2_HUMAN

This hit is scoring at : 3e-66 (expectation value)
    Alignment length (overlap) : 370
    Identities : 38 %
    Scoring matrix : BLOSUM62 (used to infer consensus pattern)
    Database searched : nrdb

```
Q:    36  CDGVVDCKLKSDELGCVRFDWDKSLLKIYSGSSHQWLPICSSNWNDSYSEKTCQQLGFES
          CDGV .C.  .DE  CVR.   .. :L::YS.....W P:C..:WN::Y....C:..:G:::
H:   133  CDGVSHCPGGEDENRCVRLYGPNFILQMYSSQRKSWHPVCQDDWNENYGRAACRDMGYKN

AHRTTEVAHRDFANSFSILRYNST      IQESLHRSE CPSQRYISLQCSHCGLRA
          . :::  .  D ..S S.:::.N::     I..:L::.S: C.S:...:SL:C  CG:..  :
          NFYSSQGIVDD SGSTSFMKLNTSAGNVDIYKKLYHSDACSSKAVVSLRCLACGVNLNSS

MTGRIVGGALASDSKWPWQVSLHFGTTHICGGTLIDAQWVLTAAHCFFVTREKVLEG---
          ...RIVGG. A ...WPWQVSLH. ..H:CGG::I...:W::TAAHC.    EK L..
          RQSRIVGGESALPGAWPWQVSLHVQNVHVCGGSIITPEWVTAAHCV    EKPLNNPWH
                                                        TRYPSIN HIS
          WKVYAGTSNLHQLPEAAS--IAEIIINSNYTDEEDDYDIALMRLSKHLTLSGEGICTP
          W..:AG.   . :  .A.  :.::I :.NY..:..: DIALM:L.KPLT.:.  : :C.P
          WTAFAGILRQSFMFYGAGYQVQKVISHPNYDSKTKNNDIALMKLQKPLTFNDLVKPVCLP

RSPAPQPQHPLQPSHLSASVNSYPGPKASADKTSPFLREVQVNLIDFKKCNDYLVYDSYL
          .     P   LQP..L .  :::  G......KTS..L...:V LI: ::CN. .VYD:.:
          N     PGMMLQPEQL-CWISGWGATEEKGKTSEVLNAAKVLLIETQRCNSRYVYDNLI

TPRMMCAGDLRGGRDSCQGDSGGPLVCEQNNRWYLAGVTSWGTGCGQRNKPGVYTKVTEV
          TP.M:CAG  L:G.  DSCQGDSGGPLV...NN W:L.G TSWG:GC:..  :PGVY .V.  .
          TPAMICAGFLQGNVDSCQGDSGGPLVTSNNNIWWLIGDTSWGSGCAKAYRPGVYGNVMVF
                                                        TRYPSIN_SER
          LPWIYSKMEA   389
          ..WIY.:M:A
          TDWIYRQMKA   490
```

FIG. 2

Prosite search results

PS00134     187->193 TRYPSIN_HIS      PDOC00124

PS00135     334->346 TRYPSIN_SER      PDOC00124

FIG. 3

BLOCKS search results

| AC# | Description | Strength | Score |
|---|---|---|---|
| BL00495N | Apple domain proteins. | 1945 | 1582 |
| AA# | 325 AGdlrGGrDsCqGDSGGPLVCeqNnRWyLaGvTSW (SEQ ID NO:15) | | |
| BL01253G | Type I fibronectin domain proteins. | 1641 | 1548 |
| AA# | 332 rDsCQGDSGGPLVC (SEQ ID NO:16) | | |
| BL00134A | Serine proteases, trypsin family, histidine p | 1500 | 1524 |
| AA# | 175 CGGTLIDAQWVLTAAHC (SEQ ID NO:17) | | |
| BL00021D | Kringle domain proteins. | 1556 | 1510 |
| AA# | 341 GPLVCEQNNRWYLaGVTSWGtGCGQRNKPGVYTKVTevLPWI (SEQ ID NO:18) | | |
| BL01253H | Type I fibronectin domain proteins. | 1765 | 1508 |
| AA# | 351 wYLaGvtSWGtGCGQRNKPGVYTKVTevLpWIysk (SEQ ID NO:19) | | |
| BL00021B | Kringle domain proteins. | 1547 | 1507 |
| AA# | 175 CGGTLIDaQWVLTAAHCF (SEQ ID NO:20) | | |
| BL004950 | Apple domain proteins. | 1756 | 1383 |
| AA# | 360 GtGCGQRnkPGVYTKVtEvlpWIysKmeA (SEQ ID NO:21) | | |
| BL00134B | Serine proteases, trypsin family, histidine p | 1289 | 1299 |
| AA# | 333 DSCQGDSGGPLVCEqNNRWYLAGV (SEQ ID NO:22) | | |
| BL01209 | LDL-receptor class A (LDLRA) domain proteins. | 1413 | 1274 |
| AA# | 35 CDGVVDCK1kSDE (SEQ ID NO:23) | | |
| BL01253F | Type I fibronectin domain proteins. | 1693 | 1270 |
| AA# | 288 AdktSpFLREvQVnLidfkKCndylVYdSylTPrMmCAG (SEQ ID NO:24) | | |
| BL00495L | Apple domain proteins. | 1947 | 1263 |
| AA# | 209 tSnlhqlpeaaSIaEIIInsNYtdeEddYDIALmrLskP (SEQ ID NO:25) | | |
| BL00134C | Serine proteases, trypsin family, histidine p | 1245 | 1254 |
| AA# | 369 PGVYTKVTEVLPWI (SEQ ID NO:26) | | |
| BL01253D | Type I fibronectin domain proteins. | 1398 | 1217 |
| AA# | 175 CGGtLIdaqWVLTA (SEQ ID NO:27) | | |

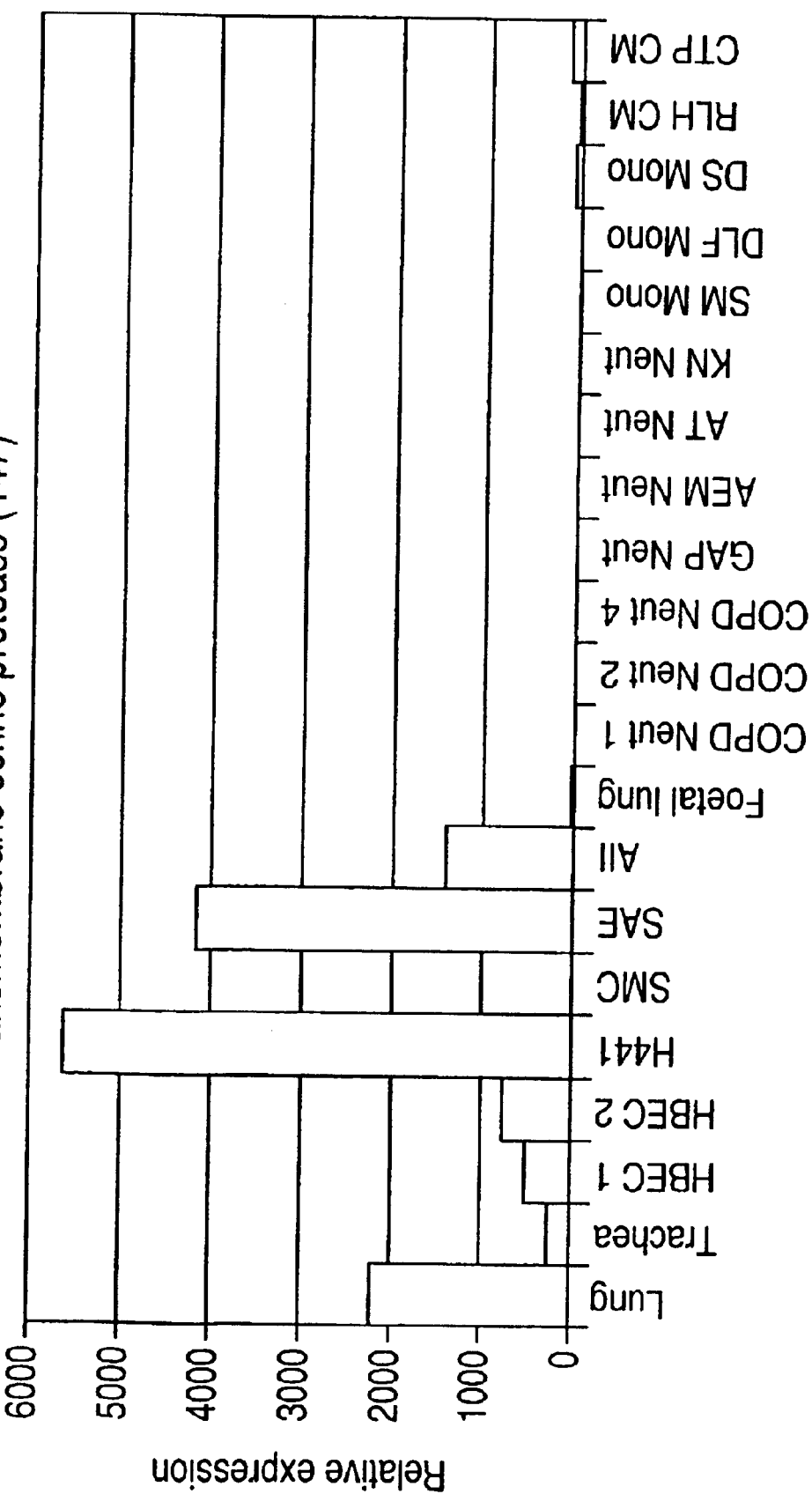

Transmembrane serine protease (147)

LBRI 147

```
                        SEQUENCE LISTING

<160> NUMBER OF SEQ ID NOS: 36

<210> SEQ ID NO 1
<211> LENGTH: 402
<212> TYPE: DNA
<213> ORGANISM: Homo sapiens
<220> FEATURE:
<221> NAME/KEY: misc_feature
<222> LOCATION: (1)...(402)
<223> OTHER INFORMATION: n = A,T,C or G

<400> SEQUENCE: 1
aatgcccttc ccagcggtat atctccctcc agtgttccca ctgcggactg agggccatga      60
ccgggcggat cgtgggaggg gcgctggcct cggatagcaa gtggccttgg caagtgagcc     120
tgcacttcgg caccacccac atctgtggag gcacgctcat tgacgcccag tgggtgctca     180
ctnccgccca ctgcttcttc gtgnacccgg gagaaggtcc tggagggctg gaaggtgtac     240
gcgggcacca gcaacctgca ccagttgcct gaggcagcct ccattgccga gatcatcatc     300
aacagcaatt acaccgatga ggaggacgac tatgacatcg ccctcatgcg gctgttcaag     360 nccccttgacc ctgttccggt gagggaattt tgcatttccc gt                       402

<210> SEQ ID NO 2
<211> LENGTH: 285
<212> TYPE: DNA
<213> ORGANISM: Homo sapiens

<400> SEQUENCE: 2
ccatgaccgg gcggatcgtg ggagggggcgc tggcctcgga tagcaagtgg ccttggcaag      60
tgagtctgca cttcggcacc acccacatct gtggaggcac gctcattgac gcccagtggg     120
tgctcactgc cgcccactgc ttcttcgtga cccgggagaa ggtcctggag ggctggaagg     180
tgtacgcggg caccagcaac ctgcaccagt tgcctgaggc agcctccatt gccgagatca     240
tcatcaacag caattacacc gatgaggagg acgactatga catcg                     285

<210> SEQ ID NO 3
<211> LENGTH: 600
<212> TYPE: DNA
<213> ORGANISM: Homo sapiens
<220> FEATURE:
```

<221> NAME/KEY: misc_feature
<222> LOCATION: (1)...(600)
<223> OTHER INFORMATION: n = A,T,C or G

<400> SEQUENCE: 3

| | | |
|---|---|---|
| gagggctgga aggtgtacgc gggcaccagc aacctgcacc agttgcctga ggcagcctcc | 60 |
| attgccgaga tcatcatcaa cagcaattac accgatgagg aggacgacta tgacatcgcc | 120 |
| ctcatgcggc tgtccaagcc cctgaccctg tccggtgagg aatctgcac tccccgctct | 180 |
| cctgcccccc agccccagca ccctctgcag ccctcgcact tgtcagcatc tgtcaactca | 240 |
| tatccgggcc ccaaagcttc tgcagggcag aagtcaaaga ctcttaaaga tccttacatg | 300 |
| gaacacttct gttttataat tagggaaact gaagcccaag ggttataaat aagtttgctc | 360 |
| caaatgacac atctcacatt acaaattgat gacggagtca gggcttgggt actgatctta | 420 |
| atcaatagat tgaattcttt cactggtatt aactgagcac ctaggggcca aacgctatgg | 480 |
| taggcatttc acacatatga tttcatttac tcttcacaac caaccctgtg gagcaggcac | 540 |
| tattattaac ttcatttgac atatgangaa atggagcttt acagagagat aattacctga | 600 |

<210> SEQ ID NO 4
<211> LENGTH: 591
<212> TYPE: DNA
<213> ORGANISM: Homo sapiens
<220> FEATURE:
<221> NAME/KEY: misc_feature
<222> LOCATION: (1)...(591)
<223> OTHER INFORMATION: n = A,T,C or G

<400> SEQUENCE: 4

| | | |
|---|---|---|
| gagggctgga aggtgtacgc gggcaccagc aacctgcacc agttgcctga ggcagcctcc | 60 |
| attgccgaga tcatcatcaa cagcaattac accgatgagg aggacgacta tgacatcgcc | 120 |
| ctcatgcggc tgtccaagcc cctgaccctg tccggtgagg aatctgcac tccccgctct | 180 |
| cctgcccccc agccccagca ccctctgcag ccctcgcact tgtcagcatc tgtcaactca | 240 |
| tatccgggcc ccaaagcttc tgcagggcag aagtcaaaga ctcttaaaga tccttacatg | 300 |
| gaacacttct gttttataat tagggaaact gaagcccaag ggttataaat aagtttgctc | 360 |
| caaatgacac atctcacatt acaaattgat gacggagtca gggcttgggt actgatctta | 420 |
| atcaatagat tgaattcttt cactggtatt aactgagcac ctaggggcca aacgctatgg | 480 |
| taggcatttc acacatatga tttcatttac tcttcacaac caaccctgtg gagcangcac | 540 |
| tattattaac ttcatttgac atatgangaa atggagcttt acagagagat a | 591 |

<210> SEQ ID NO 5
<211> LENGTH: 286
<212> TYPE: DNA
<213> ORGANISM: Homo sapiens

<400> SEQUENCE: 5

| | | |
|---|---|---|
| gcgatgtcat agtcgtcctc ctcatcggcg taattgctgt tgatgatgat ctcggcaatg | 60 |
| gaggctgcct caggcaactg gtgcaggttg ctggtgcccg cgtacacctt ccagccctcc | 120 |
| aagaccttct cccgggtcac gaagaagcag tgggcggcag tgagcaccca ctgggcgtca | 180 |
| atgagcgtgc ctccacagat gtgggtggtg ccgaagtgct gactcacttg ccaaggccac | 240 |
| ttgctattcg aggccagcgc cccttccacg attcgcccgg tcatgg | 286 |

<210> SEQ ID NO 6
<211> LENGTH: 384

```
<212> TYPE: DNA
<213> ORGANISM: Homo sapiens

<400> SEQUENCE: 6
gagggctgga aggtgtacgc gggcaccagc aacctgcacc agttgcctga ggagcctcca      60
ttgccgagat catcatcaac agcaattaca ccgatgagga ggacgactat gacatcgccc     120
tcatgcggct gtccaagccc ctgaccctgt ccggtgaggg aatctgcact ccccgctctc     180
ctgcccccca gccccagcac cctctgcagc cctcgcactt gtcagcatct gtcaactcat     240
atccggaccc caaagcttct gcagggcaga agtcaaagac tcttaaagat ccttacatgg     300
aacacttctg ttttataatt agggaaactg aagcccaagg gttataaata agtttgctcc     360
aaatgacaca tctcacatta caaa                                            384

<210> SEQ ID NO 7
<211> LENGTH: 471
<212> TYPE: DNA
<213> ORGANISM: Homo sapiens
<220> FEATURE:
<221> NAME/KEY: misc_feature
<222> LOCATION: (1)...(471)
<223> OTHER INFORMATION: n = A,T,C or G

<400> SEQUENCE: 7
tttttttttt nttttttttt ttggagcaaa cttatttana acccttgggc ttcagttncc      60
ctaattataa aacagaagtn tnccatgtaa ggnncttnaa gagtctttga cttctgccct     120
gcagaagctt tggggcccgg atatgagttg acagatgctg acaagtgcga gggctgcaga     180
gggtnctggg gctggggggc aggagagcgg ggagtgcaga ttccctcacc ggacagggtc     240
aggggnttgg acagccgcat gagggcgatg tcatagtcgt cctcctcatc ggtgtaatnn     300
ctnttgatga tgatctcggc aatggaggct gcctcaggca actgggtnca ggttnctggg     360
tncccncgta acaccttcca gccntccagg nccttttccc gggtcacgaa gaagcagtng     420
ggccgcaatt agcacccact gggggtcaat gaggctgccn ccacanattt g              471

<210> SEQ ID NO 8
<211> LENGTH: 235
<212> TYPE: DNA
<213> ORGANISM: Homo sapiens

<400> SEQUENCE: 8
gggctggaag gtgtacgcgg gcaccagcaa cctgcaccag ttgcctgagc agcctccatt      60
gccgagatca tcatcaacag caattacacc gatgaggagg acgactatga catcgccctc     120
atgcggctgt ccaagcccct gaccctgtcc ggtgagggaa tctgcactcc cgctctcct     180 gcccccagc cccagcaccc tctgcagccc tcgcacttgt cagcatctgt caact          235

<210> SEQ ID NO 9
<211> LENGTH: 19
<212> TYPE: DNA
<213> ORGANISM: Homo sapiens

<400> SEQUENCE: 9
ctgccagcag ctgggtttc                                                   19

<210> SEQ ID NO 10
<211> LENGTH: 20
<212> TYPE: DNA
<213> ORGANISM: Homo sapiens
```

<400> SEQUENCE: 10
aggctttcct ggatggtgga                                                20

<210> SEQ ID NO 11
<211> LENGTH: 1748
<212> TYPE: DNA
<213> ORGANISM: Homo sapiens

<400> SEQUENCE: 11

| | | | | | |
|---|---|---|---|---|---|
| ctcagagacc | atggagaggg | acagccacgg | gaatgcatct | ccagcaagaa | caccttcagc | 60 |
| tggagcatct | ccagcccagg | catctccagc | tgggacacct | ccaggccggg | catctccagc | 120 |
| ccaggcatct | ccagcccagg | catctccagc | tgggacacct | ccgggccggg | catctccagc | 180 |
| ccaggcatct | ccagctggta | cacctccagg | ccggcatct | ccaggccggg | catctccagc | 240 |
| ccaggcatct | ccagcccggg | catctccggc | tctggcatca | ctttccaggt | cctcatccgg | 300 |
| caggtcatca | tccgccaggt | cagcctcggt | gacaacctcc | ccaaccagag | tgtaccttgt | 360 |
| tagagcaaca | ccagtggggg | ctgtacccat | ccgatcatct | cctgccaggt | cagcaccagc | 420 |
| aaccagggcc | accagggaga | gcccaggtac | gagcctgccc | aagttcacct | ggcgggaggg | 480 |
| ccagaagcag | ctaccgctca | tcgggtgcgt | gctcctcctc | attgccctgg | tggtttcgct | 540 |
| catcatcctc | ttccagttct | ggcagggcca | cacagggatc | aggtacaagg | agcagaggga | 600 |
| gagctgtccc | aagcacgctg | ttcgctgtga | cggggtggtg | gactgcaagc | tgaagagtga | 660 |
| cgagctgggc | tgcgtgaggt | ttgactggga | caagtctctg | cttaaaatct | actctgggtc | 720 |
| ctcccatcag | tggcttccca | tctgtagcag | caactggaat | gactcctact | cagagaagac | 780 |
| ctgccagcag | ctgggtttcg | agagtgctca | ccggacaacc | gaggttgccc | acagggattt | 840 |
| tgccaacagc | ttctcaatct | tgagatacaa | ctccaccatc | caggaaagcc | tccacaggtc | 900 |
| tgaatgccct | tccagcggt | atatctccct | ccagtgttcc | cactgcggac | tgagggccat | 960 |
| gaccgggcgg | atcgtgggag | gggcgctggc | ctcggatagc | aagtggcctt | ggcaagtgag | 1020 |
| tctgcacttc | ggcaccaccc | acatctgtgg | aggcacgctc | attgacgccc | agtgggtgct | 1080 |
| cactgccgcc | cactgcttct | tcgtgacccg | ggagaaggtc | ctggagggct | ggaaggtgta | 1140 |
| cgcgggcacc | agcaacctgc | accagttgcc | tgaggcagcc | tccattgccg | agatcatcat | 1200 |
| caacagcaat | tacaccgatg | aggaggacga | ctatgacatc | gccctcatgc | ggctgtccaa | 1260 |
| gccccctgacc | ctgtccgctc | acatccaccc | tgcttgcctc | cccatgcatg | gacagacctt | 1320 |
| tagcctcaat | gagacctgct | ggatcacagg | ctttggcaag | accagggaga | cagatgacaa | 1380 |
| gacatccccc | ttcctccggg | aggtgcaggt | caatctcatc | gacttcaaga | atgcaatga | 1440 |
| ctacttggtc | tatgacagtt | accttacccc | aaggatgatg | tgtgctgggg | accttcgtgg | 1500 |
| gggcagagac | tcctgccagg | gagacagcgg | ggggcctctt | gtctgtgagc | agaacaaccg | 1560 |
| ctggtacctg | gcaggtgtca | ccagctgggg | cacaggctgt | ggccagagaa | acaaacctgg | 1620 |
| tgtgtacacc | aaagtgacag | aagttcttcc | ctggatttac | agcaagatgg | agagcgaggt | 1680 |
| gcgattcaga | aaatcctaac | cagctggcct | gctgctctgc | acagcaccgg | ctgctgtgac | 1740 |
| tcgagaaa | | | | | | 1748 |

<210> SEQ ID NO 12
<211> LENGTH: 562
<212> TYPE: PRT
<213> ORGANISM: Homo sapiens

<400> SEQUENCE: 12

```
Met Glu Arg Asp Ser His Gly Asn Ala Ser Pro Ala Arg Thr Pro Ser
 1               5                  10                 15

Ala Gly Ala Ser Pro Ala Gln Ala Ser Pro Ala Gly Thr Pro Pro Gly
            20                  25                 30

Arg Ala Ser Pro Ala Gln Ala Ser Pro Ala Gln Ala Ser Pro Ala Gly
            35                  40                  45

Thr Pro Pro Gly Arg Ala Ser Pro Ala Gln Ala Ser Pro Ala Gly Thr
        50                  55                  60

Pro Pro Gly Arg Ala Ser Pro Gly Arg Ala Ser Pro Ala Gln Ala Ser
 65                  70                  75                 80

Pro Ala Arg Ala Ser Pro Ala Leu Ala Ser Leu Ser Arg Ser Ser Ser
                85                  90                  95

Gly Arg Ser Ser Ser Ala Arg Ser Ala Ser Val Thr Thr Ser Pro Thr
            100                 105                 110

Arg Val Tyr Leu Val Arg Ala Thr Pro Val Gly Ala Val Pro Ile Arg
            115                 120                 125

Ser Ser Pro Ala Arg Ser Ala Pro Ala Thr Arg Ala Thr Arg Glu Ser
    130                 135                 140

Pro Gly Thr Ser Leu Pro Lys Phe Thr Trp Arg Glu Gly Gln Lys Gln
145                 150                 155                 160

Leu Pro Leu Ile Gly Cys Val Leu Leu Ile Ala Leu Val Val Ser
                165                 170                 175

Leu Ile Ile Leu Phe Gln Phe Trp Gln Gly His Thr Gly Ile Arg Tyr
                180                 185                 190

Lys Glu Gln Arg Glu Ser Cys Pro Lys His Ala Val Arg Cys Asp Gly
            195                 200                 205

Val Val Asp Cys Lys Leu Lys Ser Asp Glu Leu Gly Cys Val Arg Phe
    210                 215                 220

Asp Trp Asp Lys Ser Leu Leu Lys Ile Tyr Ser Gly Ser Ser His Gln
225                 230                 235                 240

Trp Leu Pro Ile Cys Ser Ser Asn Trp Asn Asp Ser Tyr Ser Glu Lys
                245                 250                 255

Thr Cys Gln Gln Leu Gly Phe Glu Ser Ala His Arg Thr Thr Glu Val
            260                 265                 270

Ala His Arg Asp Phe Ala Asn Ser Phe Ser Ile Leu Arg Tyr Asn Ser
    275                 280                 285

Thr Ile Gln Glu Ser Leu His Arg Ser Glu Cys Pro Ser Gln Arg Tyr
            290                 295                 300

Ile Ser Leu Gln Cys Ser His Cys Gly Leu Arg Ala Met Thr Gly Arg
305                 310                 315                 320

Ile Val Gly Gly Ala Leu Ala Ser Asp Ser Lys Trp Pro Trp Gln Val
            325                 330                 335

Ser Leu His Phe Gly Thr Thr His Ile Cys Gly Gly Thr Leu Ile Asp
            340                 345                 350

Ala Gln Trp Val Leu Thr Ala Ala His Cys Phe Phe Val Thr Arg Glu
            355                 360                 365

Lys Val Leu Glu Gly Trp Lys Val Tyr Ala Gly Thr Ser Asn Leu His
            370                 375                 380

Gln Leu Pro Glu Ala Ala Ser Ile Ala Glu Ile Ile Asn Ser Asn
385                 390                 395                 400

Tyr Thr Asp Glu Glu Asp Tyr Asp Ile Ala Leu Met Arg Leu Ser
                405                 410                 415
```

```
Lys Pro Leu Thr Leu Ser Ala His Ile His Pro Ala Cys Leu Pro Met
            420                 425                 430

His Gly Gln Thr Phe Ser Leu Asn Glu Thr Cys Trp Ile Thr Gly Phe
            435                 440                 445

Gly Lys Thr Arg Glu Thr Asp Asp Lys Thr Ser Pro Phe Leu Arg Glu
            450                 455                 460

Val Gln Val Asn Leu Ile Asp Phe Lys Lys Cys Asn Asp Tyr Leu Val
465                 470                 475                 480

Tyr Asp Ser Tyr Leu Thr Pro Arg Met Met Cys Ala Gly Asp Leu Arg
                485                 490                 495

Gly Gly Arg Asp Ser Cys Gln Gly Asp Ser Gly Gly Pro Leu Val Cys
            500                 505                 510

Glu Gln Asn Asn Arg Trp Tyr Leu Ala Gly Val Thr Ser Trp Gly Thr
            515                 520                 525

Gly Cys Gly Gln Arg Asn Lys Pro Gly Val Tyr Thr Lys Val Thr Glu
            530                 535                 540

Val Leu Pro Trp Ile Tyr Ser Lys Met Glu Ser Glu Val Arg Phe Arg
545                 550                 555                 560

Lys Ser

<210> SEQ ID NO 13
<211> LENGTH: 27
<212> TYPE: DNA
<213> ORGANISM: Homo sapiens

<400> SEQUENCE: 13
caacctcggt tgtccggtga gcactct                                            27

<210> SEQ ID NO 14
<211> LENGTH: 492
<212> TYPE: PRT
<213> ORGANISM: Homo sapiens

<400> SEQUENCE: 14

Met Ala Leu Asn Ser Gly Ser Pro Pro Ala Ile Gly Pro Tyr Tyr Glu
  1               5                  10                  15

Asn His Gly Tyr Gln Pro Glu Asn Pro Tyr Pro Ala Gln Pro Thr Val
             20                  25                  30

Val Pro Thr Val Tyr Glu Val His Pro Ala Gln Tyr Tyr Pro Ser Pro
            35                  40                  45

Val Pro Gln Tyr Ala Pro Arg Val Leu Thr Gln Ala Ser Asn Pro Val
 50                  55                  60

Val Cys Thr Gln Pro Lys Ser Pro Ser Gly Thr Val Cys Thr Ser Lys
 65                  70                  75                  80

Thr Lys Lys Ala Leu Cys Ile Thr Leu Thr Leu Gly Thr Phe Leu Val
                 85                  90                  95

Gly Ala Ala Leu Ala Ala Gly Leu Leu Trp Lys Phe Met Gly Ser Lys
            100                 105                 110

Cys Ser Asn Ser Gly Ile Glu Cys Asp Ser Ser Gly Thr Cys Ile Asn
            115                 120                 125

Pro Ser Asn Trp Cys Asp Gly Val Ser His Cys Pro Gly Gly Glu Asp
            130                 135                 140

Glu Asn Arg Cys Val Arg Leu Tyr Gly Pro Asn Phe Ile Leu Gln Met
145                 150                 155                 160

Tyr Ser Ser Gln Arg Lys Ser Trp His Pro Val Cys Gln Asp Asp Trp
                165                 170                 175
```

```
Asn Glu Asn Tyr Gly Arg Ala Ala Cys Arg Asp Met Gly Tyr Lys Asn
            180                 185                 190

Asn Phe Tyr Ser Ser Gln Gly Ile Val Asp Asp Ser Gly Ser Thr Ser
        195                 200                 205

Phe Met Lys Leu Asn Thr Ser Ala Gly Asn Val Asp Ile Tyr Lys Lys
    210                 215                 220

Leu Tyr His Ser Asp Ala Cys Ser Ser Lys Ala Val Val Ser Leu Arg
225                 230                 235                 240

Cys Leu Ala Cys Gly Val Asn Leu Asn Ser Ser Arg Gln Ser Arg Ile
                245                 250                 255

Val Gly Gly Glu Ser Ala Leu Pro Gly Ala Trp Pro Trp Gln Val Ser
            260                 265                 270

Leu His Val Gln Asn Val His Val Cys Gly Gly Ser Ile Ile Thr Pro
        275                 280                 285

Glu Trp Ile Val Thr Ala Ala His Cys Val Glu Lys Pro Leu Asn Asn
    290                 295                 300

Pro Trp His Trp Thr Ala Phe Ala Gly Ile Leu Arg Gln Ser Phe Met
305                 310                 315                 320

Phe Tyr Gly Ala Gly Tyr Gln Val Gln Lys Val Ile Ser His Pro Asn
                325                 330                 335

Tyr Asp Ser Lys Thr Lys Asn Asn Asp Ile Ala Leu Met Lys Leu Gln
            340                 345                 350

Lys Pro Leu Thr Phe Asn Asp Leu Val Lys Pro Val Cys Leu Pro Asn
        355                 360                 365

Pro Gly Met Met Leu Gln Pro Glu Gln Leu Cys Trp Ile Ser Gly Trp
370                 375                 380

Gly Ala Thr Glu Glu Lys Gly Lys Thr Ser Glu Val Leu Asn Ala Ala
385                 390                 395                 400

Lys Val Leu Leu Ile Glu Thr Gln Arg Cys Asn Ser Arg Tyr Val Tyr
                405                 410                 415

Asp Asn Leu Ile Thr Pro Ala Met Ile Cys Ala Gly Phe Leu Gln Gly
            420                 425                 430

Asn Val Asp Ser Cys Gln Gly Asp Ser Gly Gly Pro Leu Val Thr Ser
        435                 440                 445

Asn Asn Asn Ile Trp Trp Leu Ile Gly Asp Thr Ser Trp Gly Ser Gly
    450                 455                 460

Cys Ala Lys Ala Tyr Arg Pro Gly Val Tyr Gly Asn Val Met Val Phe
465                 470                 475                 480

Thr Asp Trp Ile Tyr Arg Gln Met Lys Ala Asn Gly
                485                 490

<210> SEQ ID NO 15
<211> LENGTH: 23
<212> TYPE: PRT
<213> ORGANISM: Artificial Sequence
<220> FEATURE:
<223> OTHER INFORMATION: BLOCKS BL00495

<400> SEQUENCE: 15

Ala Gly Gly Gly Asp Cys Gly Asp Ser Gly Gly Pro Leu Val Cys Asn
 1               5                  10                  15

Arg Trp Leu Gly Thr Ser Trp
            20

<210> SEQ ID NO 16
```

```
<211> LENGTH: 12
<212> TYPE: PRT
<213> ORGANISM: Artificial Sequence
<220> FEATURE:
<223> OTHER INFORMATION: BLOCKS BL1253G

<400> SEQUENCE: 16

Asp Cys Gln Gly Asp Ser Gly Gly Pro Leu Val Cys
 1               5                  10

<210> SEQ ID NO 17
<211> LENGTH: 17
<212> TYPE: PRT
<213> ORGANISM: Artificial Sequence
<220> FEATURE:
<223> OTHER INFORMATION: BLOCKS BL00134A

<400> SEQUENCE: 17

Cys Gly Gly Thr Leu Ile Asp Ala Gln Trp Val Leu Thr Ala Ala His
 1               5                  10                  15

Cys

<210> SEQ ID NO 18
<211> LENGTH: 38
<212> TYPE: PRT
<213> ORGANISM: Artificial Sequence
<220> FEATURE:
<223> OTHER INFORMATION: BLOCKS BL00021D

<400> SEQUENCE: 18

Gly Pro Leu Val Cys Glu Gln Asn Asn Arg Trp Tyr Leu Val Thr
 1               5                  10                  15

Ser Trp Gly Gly Cys Gly Gln Arg Asn Lys Pro Gly Val Tyr Thr Lys
             20                  25                  30

Val Thr Leu Pro Trp Ile
             35

<210> SEQ ID NO 19
<211> LENGTH: 24
<212> TYPE: PRT
<213> ORGANISM: Artificial Sequence
<220> FEATURE:
<223> OTHER INFORMATION: BLOCKS BL01243H

<400> SEQUENCE: 19

Tyr Leu Gly Ser Trp Gly Gly Cys Gly Gln Arg Asn Lys Pro Gly Val
 1               5                  10                  15

Tyr Thr Lys Val Thr Leu Trp Ile
             20

<210> SEQ ID NO 20
<211> LENGTH: 17
<212> TYPE: PRT
<213> ORGANISM: Artificial Sequence
<220> FEATURE:
<223> OTHER INFORMATION: BLOCKS BL00021B

<400> SEQUENCE: 20

Cys Gly Gly Thr Leu Ile Asp Gln Trp Val Leu Thr Ala Ala His Cys
 1               5                  10                  15

Phe

<210> SEQ ID NO 21
<211> LENGTH: 18
```

```
<212> TYPE: PRT
<213> ORGANISM: Artificial Sequence
<220> FEATURE:
<223> OTHER INFORMATION: BLOCKS BL004950

<400> SEQUENCE: 21

Gly Gly Cys Gly Gln Arg Pro Gly Val Tyr Thr Lys Val Glu Trp Ile
 1               5                  10                  15

Lys Ala

<210> SEQ ID NO 22
<211> LENGTH: 23
<212> TYPE: PRT
<213> ORGANISM: Artificial Sequence
<220> FEATURE:
<223> OTHER INFORMATION: BLOCKS BL00134B

<400> SEQUENCE: 22

Asp Ser Cys Gln Gly Asp Ser Gly Gly Pro Leu Val Cys Glu Asn Asn
 1               5                  10                  15

Arg Trp Tyr Leu Ala Gly Val
            20

<210> SEQ ID NO 23
<211> LENGTH: 12
<212> TYPE: PRT
<213> ORGANISM: Artificial Sequence
<220> FEATURE:
<223> OTHER INFORMATION: BLOCKS BL01209

<400> SEQUENCE: 23

Cys Asp Gly Val Val Asp Cys Lys Lys Ser Asp Glu
 1               5                  10

<210> SEQ ID NO 24
<211> LENGTH: 20
<212> TYPE: PRT
<213> ORGANISM: Artificial Sequence
<220> FEATURE:
<223> OTHER INFORMATION: BLOCKS BL01253F

<400> SEQUENCE: 24

Ala Ser Phe Leu Arg Glu Gln Val Leu Lys Cys Val Tyr Ser Thr Pro
 1               5                  10                  15

Met Cys Ala Gly
            20

<210> SEQ ID NO 25
<211> LENGTH: 17
<212> TYPE: PRT
<213> ORGANISM: Artificial Sequence
<220> FEATURE:
<223> OTHER INFORMATION: BLOCKS BL00495L

<400> SEQUENCE: 25

Ser Ser Ile Glu Ile Ile Ile Asn Tyr Glu Tyr Asp Ile Ala Leu Leu
 1               5                  10                  15
Pro

<210> SEQ ID NO 26
<211> LENGTH: 14
<212> TYPE: PRT
<213> ORGANISM: Artificial Sequence
<220> FEATURE:
<223> OTHER INFORMATION: BLOCKS BL00134C
```

-continued

```
<400> SEQUENCE: 26

Pro Gly Val Tyr Thr Lys Val Thr Glu Val Leu Pro Trp Ile
 1               5                  10

<210> SEQ ID NO 27
<211> LENGTH: 10
<212> TYPE: PRT
<213> ORGANISM: Artificial Sequence
<220> FEATURE:
<223> OTHER INFORMATION: BLOCKS BL01253D

<400> SEQUENCE: 27

Cys Gly Gly Leu Ile Trp Val Leu Thr Ala
 1               5                  10

<210> SEQ ID NO 28
<211> LENGTH: 834
<212> TYPE: DNA
<213> ORGANISM: Homo sapiens

<400> SEQUENCE: 28
gctgggctgc gtgaggtttg actgggacaa gtctctgctt aaaatctact ctgggtcctc      60
ccatcagtgg cttcccatct gtagcagcaa ctggaatgac tcctactcag agaagacctg     120
ccagcagctg ggtttcgaga gtgctcaccg acaaccgag gttgcccaca gggattttgc      180
caacagcttc tcaatcttga gatacaactc caccatccag gaaagcctcc acaggtctga     240
atgcccttcc cagcggtata tctccctcca gtgttccac tgcggactga gggccatgac      300
cgggcggatc gtgggagggg cgctggcctc ggatagcaag tggccttggc aagtgagtct     360
gcacttcggc accacccaca tctgtggagg cacgctcatt gacgcccagt gggtgctcac     420
tgccgcccac tgcttcttcg tgacccggga aaggtcctg gagggctgga aggtgtacgc      480
gggcaccagc aactgcacca gttgcctgag gcagctccat gccgagatc atcatcaaca     540 gcaattacac cgatgaggag gacgactatt gacatcgccc tcatgcggct gttccaagcc    600
cctgaacctg tccgtcacat ccaccctgct tgcctcccc atgcatggac agacctttag    660
cctcaatgag acctgttgga tcacaggctt tggcaaagac agggagacag atgaaaagac    720
atcccccttc ctcgggaggt gcaggtcaat ctcatcgact tccagaaatg caatgactaa    780
ctggtctatg acagtacctt acccaaggat gatgtgtgtg gggaacttcg tggg           834

<210> SEQ ID NO 29
<211> LENGTH: 621
<212> TYPE: DNA
<213> ORGANISM: mouse

<400> SEQUENCE: 29
agatcatcat ctgccaggtc agcctccacg acatcctccc caacgagagt gtaccttgtt      60
agagcaacac cagtggggc tgtccccatc cgggcatctc ctgccaggtc agcaccagcc     120
accagggcca ccagggtaga gcccaggtct cagtttcccc aagttctcct ggtcaggaga    180
cccagaggca gctgccactc atcgggtgtg tcatccttct catcagcctg gtgatctcgc    240
tcatccttct cttctacttc tggagagtgc cacacaggga tcaagtacaa agagccactg    300
gagagttgcc ctatccacgc agttcgctgt gatggagtgg tggacttgca aaatgaagag    360
cgatgagctg ggctgtgtca ggttcgactg ggacaagtcc ctcctgaaag tctactctgg    420
gtcttctggc agagtggctt cctgtctgca gcagcagcgg aacgacactg actccaagag    480
gacctgccag caagctggga tttgacagcg cttaccgaac aactgaggta gcccacagag    540
```

```
acatcaccag cagcttctaa ctctcggaaa caaaacaaca tccaggaaag gctctacagg    600
tcgaatgtct tccggcggat g                                              621

<210> SEQ ID NO 30
<211> LENGTH: 678
<212> TYPE: DNA
<213> ORGANISM: mouse

<400> SEQUENCE: 30
tcagcctcca cgacatcctc cccaacgaga gtgtaccttg ttagagcaac accagtgggg     60
gctgtcccca tccgggcatc tcctgccagg tcagcaccag ccaccagggc caccagggag    120
agcccaggtc tcagtttccc caagttctcc tggcaggaga cccagaggca gctgccactc    180
atcgggtgtg tcatccttct catcagcctg gtgatctcgc tcatccttct cttctacttc    240
tggagaggcc acacagggat caagtacaaa gagccactgg agagttgccc tatccacgca    300
gttcgctgtg atggagtggt ggactgcaaa atgaagagcg atgagctggg ctgtgtcagg    360
ttcgactggg acaagtccct cctgaaagtc tactctgggt cttctggcga gtggcttcct    420
gtctgcagca gcagctggaa cgacactgac tccaagagga cctgccagca gctgggattt    480
gacagcgctt accgaacaac tgaggtagcc cacaggaaca tcaccagcag cttcttactc    540
tccgaataca acaccaccat ccaggaaagc ctctacaggt cgcaatgtcc ttccggcggt    600
atgtctccct ccagtgttcc cacgtggttt ggagctatga cgggcggacg aggagggtc    660 gacctcgaag catgcctg                                                  678

<210> SEQ ID NO 31
<211> LENGTH: 577
<212> TYPE: DNA
<213> ORGANISM: mouse

<400> SEQUENCE: 31
aagttttgat tacgcgcttt ctgcaattga tctcttgtta tttaaaccaa cggtttcagg     60
tcaatctttg gagtatttgt agcttctaat ttttgaaatg actgaattaa gaatttggat    120
gcttgctctt ttggttggtt tgcctaaaat ccagcccaca atccagtcgt ctcttgggag    180
agggaggtgc cttgcaaact ttcatataac gaatgtgcct gaggctgctt aactctggac    240
tagtctcaga tctcaaacct gcactacacg aggaggcata cttttgcttc atctggacat    300
ttagaatact gtaaccttgc tgccgttctg ttagattgct aactacgtcc cccgtctcca    360
atttggctct ccttaggcga taggatttgt cgttttttaac ggcaataaac ttgacaacac    420
cagaatccaa gttttacttg aaaagctcgg cagaatacag agtggtgtga caaaaaacaa    480
cagcaaaggg ttcctttgtg caatgacaaa cggtaaaaat gctgtaacgt tgaagaataa    540
ctatttccac gcaagaacct cctgcttgac tgtgtat                             577

<210> SEQ ID NO 32
<211> LENGTH: 688
<212> TYPE: DNA
<213> ORGANISM: mouse

<400> SEQUENCE: 32
ggtgatctcg ctccatccgt tctcttctac ttctggagag tgccacacac gggatcaagt     60
acaacggagc cactggagag ttgccctatc cacgcagttc gctgtgatgg agtggtggac    120
tgcaaaatga agcagcgata gagctgggct gtgtcaggtt cgactgggac aagtccctcc    180
```

```
tgaaagtcta ctctgggtct tctggcgagt ggcttcctgt ctgcagcagc gagctggaac      240
gacactgact ccaagaggac ctgccagcag ctgggattct gacagcgctt accgaacaac      300
tgaggtagcc cactagagac tgtcaccagc agcttcttga ctctccgaat acgacaccac      360
caatccagga aagcctctac aggtcgcaat atccttcccg gcggtaatgg tctcccatcc      420
agtgttccca ctgtggtttg agagcctatg accgggcgga tcgtgggagg cggctctgaa      480
cctcggagag caagtgcgcc ctggctaagt tagcctgcac ttcggcaact acccacattc      540
tgtggcggca cacttcatcg atagcccagt gtgttctcca ccggttgcca ccgttttttg      600 tgacccccgca acaacctctt aacaagtgac aacacctttt tccaccacaa atgtcccacg      660
acccacaagt ccttctcccc aactcttg                                         688

<210> SEQ ID NO 33
<211> LENGTH: 614
<212> TYPE: DNA
<213> ORGANISM: mouse

<400> SEQUENCE: 33
ccagatcatc atcaacggca actacacaga tgaacaggat gactatgaca ttgccctcat       60
caggctgtcc aagcccctga ccctgtcagc tcacatccac cctgcctgcc tcccgatgca      120
cggtcagacc ttcggcctca atgagacctg tggatcacgg gcttggcaaa accaaggaga      180
cagatgagaa gacatctccc ttcctccgag aggttcaggt caacctcatt gacttcaaga      240
agtgcaatga ctacttggtc tatgacagct accttacccc aaggatgatg tgtgccgggg      300
atctacgagg agggagggac tcctgccagg gagacagtgg aggacctctc gtctgtgagc      360
agaacaatcg ctggtacctg gcaggtgtca ccagctgggg cacaggctgt ggccagaaaa      420
acaagcctgg tgtgtacacc aaagtgacag aagtacttcc ctggatttac agaaagatgg      480
agagtgaggt acgattccgg aaatcttaac catgtcctcc tcacgtagct gactgctatg      540
aagatcctgg gcacagggat ggggccattt gcagccatct ggtacagtgg acaacaagca      600
cctttggttc tccc                                                         614

<210> SEQ ID NO 34
<211> LENGTH: 751
<212> TYPE: DNA
<213> ORGANISM: Homo sapiens

<400> SEQUENCE: 34
aagcctggag gactcttccc ctcagagacc atggagaggg acagccacgg gaatgcatct       60
ccagcaagaa caccttcaga ctggagcatc tccagcccag gcatctccag ctgggacacc      120
tccaggccgg gcatctccag cccaggcatc actttccagg tcctcatcct ggcaggtcat      180
catccgccag gtcagcctcg gtgacaacct ccccaaccag agtgtacctt gttagagcaa      240
caccagtggg ggctgtaccc atccgatcat ctcctgccag gtcagcacca gcaaccaggg      300
ccacagtgga gagcccaggt acgagcctga ccaagttcaa ctgagcaggg agggccagaa      360
gcagctaccg actcatcgga gtgcagtgct cactcctcat tgccctggat ggtttacgct      420
catcatcctc ttccagttct ggcagggcac acagggatca aggtcacaag gagcaagatg      480
tgtgagagct tgtcccaaag cacgcctgtt cgcttgtgca cggggtgtat gggacttcca      540
aagactgaag aggtgacaga cgctgtgcta gcgtgaggta ttgactggga ccaacgtctc      600
tgctttaaaa tcttactctg gtccctccaa atcagtggga tcccatctgt agcagcacct      660
gggaattgac tctactacag agaagactgc cagcgagtgg gatcaaagag gtccccggga      720
```

```
cacgaggtgg ccacaggatt ggcaaagatt a                              751
```

<210> SEQ ID NO 35
<211> LENGTH: 1230
<212> TYPE: DNA
<213> ORGANISM: Homo sapiens
<220> FEATURE:
<221> NAME/KEY: misc_feature
<222> LOCATION: (1)...(1230)
<223> OTHER INFORMATION: n = A,T,C or G

<400> SEQUENCE: 35

```
atgacccagc tgtctgcttc tttttctcta gtccagttct ggcagnncca cacagnnatc    60
aggtacaagg agcagaggga gagctgtccc aagcacgctg ttcgctgtga cggggtggtg   120
gactgcaagc tgaagagtga cgagctgggc tgcgtgaggt ttgactggga caagtctctg   180
cttaaaatct actctgggtc ctcccatcag tggcttccca tctgtagcag caactggaat   240
gactcctact cagagaagac ctgccagcag ctgggtttcg agagtgctca ccggacaacc   300
gaggttgccc acagggattt tgccaacagc ttctcaatct tgagatacaa ctccaccatc   360
caggaaagcc tccacaggtc tgaatgccct tcccagcggt atatctctct ccagtgttcc   420
cactgcggac tgagggccat gaccggcggg atcgtgggag gggcgctggc ctcggatagc   480
aagtggcctt ggcaagtgag tctgcacttc ggcaccaccc acatctgtgg aggcacgctc   540
attgacgccc agtgggtgct cactgccgcc cactgcttct tcgtgacccg ggagaaggtc   600
ctggagggct ggaaggtgta cgcgggcacc agcaacctgc accagttgcc tgaggcagcc   660
tccattgccg agatcatcat caacagcaat tacaccgatg aggaggacga ctatgacatc   720
gccctcatgc ggctgtccaa gcccctgacc ctgtccggtg agggaatctg cactccccgc   780
tctcctgccc cccagcccca gcaccctctg cagccctcgc acttgtcagc atctgtcaac   840
tcatatccgg gccccaaagc ttctgcagac aagacatccc ccttcctccg ggaggtgcag   900
gtcaatctca tcgacttcaa gaaatgcaat gactacttgg tctatgacag ttaccttacc   960
ccaaggatga tgtgtgctgg ggaccttcgt gggggcagag actcctgcca gggagacagc  1020
gggggggcctc ttgtctgtga gcagaacaac cgctggtacc tggcaggtgt caccagctgg  1080
ggcacaggct gtggccagag aaacaaacct ggtgtgtaca ccaaagtgac agaagttctt  1140
ccctggattt acagcaagat ggaggcgagg tgcgattcag aaaatcctaa ccagctggcc  1200
tgctgctctg cacagcaccg gctgctgtga                                   1230
```

<210> SEQ ID NO 36
<211> LENGTH: 24
<212> TYPE: DNA
<213> ORGANISM: Artificial Sequence
<220> FEATURE:
<223> OTHER INFORMATION: Random oligonucleotide

<400> SEQUENCE: 36

```
tcaactgact agatgtacat ggac                                         24
```

US 6,734,006 B2

REGULATION OF HUMAN TRANSMEMBRANE SERINE PROTEASE

This application claims the benefit of and incorporates by reference co-pending provisional applications Ser. No. 60/211,224 filed Jun. 13, 2000, Ser. No. 60/283,353 filed Apr. 13, 2001, and Ser. No. 60/283,648 filed Apr. 16, 2001, and PCT application PCT/EP01/06618 filed Jun. 12, 2001.

TECHNICAL FIELD OF THE INVENTION

The invention relates to the area of regulation human transmembrane serine protease activity to provide therapeutic effects.

BACKGROUND OF THE INVENTION

Metastasizing cancer cells invade the extracellular matrix using plasma membrane protrusions that contact and dissolve the matrix with proteases. Agents that inhibit such protease activity can be used to suppress metastases. Proteases also are expressed during development, when degradation of the extracellular matrix is desired. In cases where appropriate extracellular matrix degradation does not occur, supplying a molecule with a protease activity can provide the necessary enzymatic activity. Thus, there is a need in the art for identifying new proteases and methods of regulating extracellular matrix degradation.

SUMMARY OF THE INVENTION

It is an object of the invention to provide reagents and methods of regulating human transmembrane serine protease. These and other objects of the invention are provided by one or more of the embodiments described below.

One embodiment of the invention is a cDNA encoding a polypeptide comprising an amino acid sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof.

Yet another embodiment of the invention is an expression vector comprising a polynucleotide which encodes a polypeptide comprising an amino acid sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof.

Another embodiment of the invention is a host cell comprising an expression vector which encodes a polypeptide comprising an amino acid sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof.

Still another embodiment of the invention is a purified polypeptide comprising an ammo acid sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof.

Even another embodiment of the invention is a fusion protein comprising a polypeptide consisting of an amino acid sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof.

Another embodiment of the invention is a method of producing a polypeptide comprising an amino acid sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof. A host cell comprising an expression vector that encodes the polypeptide is cultured under conditions whereby the polypeptide is expressed. The polypeptide is isolated.

Yet another embodiment of the invention is a method of detecting a coding sequence for a polypeptide comprising an amino acid sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof. A polynucleotide comprising 11 contiguous nucleotides selected from the group consisting of (a) the complement of the nucleotide sequence shown in SEQ ID NO:11, (b) the complement of the coding sequence of the cDNA insert of plasmid pCRII-TMSP3, (c) a polynucleotide that hybridizes under stringent conditions to (a) or (b), (d) a polynucleotide having a nucleic acid sequence that deviates from the nucleic acid sequences specified in (a) to (c) due to the degeneration of the genetic code, and (e) a polynucleotide that represents a fragment, derivative, or allelic variation of a nucleic acid sequence specified in (a) to (d) is hybridized to nucleic acid material of a biological sample to form a hybridization complex. The hybridization complex is detected.

Even another embodiment of the invention is a kit far detecting a coding sequence for a polypeptide comprising an amino acid sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof. The kit comprises a polynucleotide and instructions for detecting the coding sequence. The polynucleotide comprises 11 contiguous nucleotides selected from the group consisting of (a) the complement of the nucleotide sequence shown in SEQ ID NO:11, (b) the complement of the coding sequence of the cDNA insert of plasmid pCRII-TMSP3 to nucleic acid material of a biological sample to form a hybridization complex, (c) a polynucleotide that hybridizes under stringent conditions to (a) or (b), (d) a polynucleotide having a nucleic acid sequence that deviates from the nucleic acid sequences specified in (a) to (c) due to the degeneration of the genetic code, and (e) a polynucleotide that represents a fragment, derivative, or allelic variation of a nucleic acid sequence specified in (a) to (d).

Still another embodiment of the invention is a method of detecting a polypeptide comprising an amino acid sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof. A biological sample is contacted with a reagent that specifically binds to the polypeptide to form a reagent-polypeptide complex. The reagent-polypeptide complex is detected.

Yet another embodiment of the invention is a kit for detecting a polypeptide comprising an amino acid sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof. The kit comprises an antibody which specifically binds to the polypeptide and instructions for detecting the polypeptide.

Even another embodiment of the invention is a method of screening for agents that can regulate an activity of a human transmembrane serine protease. A test compound is contacted with a polypeptide comprising an amino acid sequence selected from the group consisting of: (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof. Binding of the test compound to the polypeptide is detected. A test compound that binds to the polypeptide is thereby identified as a potential agent for regulating the activity of the human transmembrane serine protease.

A further embodiment of the invention is a method of screening for therapeutic agents that can regulate an enzymatic activity of a human transmembrane serine protease. A test compound is contacted with a polypeptide comprising an amino acid sequence selected from the group consisting of: (a) the amino acid sequence shown in SEQ ID NO:12, (b) the amino acid sequence encoded by a cDNA insert contained within plasmid pCRII-TMSP3 (ATCC Accession No. PTA-3433), end (c) biologically active variants thereof. The enzymatic activity of the polypeptide is detected. A test compound that increases the enzymatic activity of the polypeptide is thereby identified as a potential therapeutic agent for increasing the enzymatic activity of the human transmembrane serine protease. A test compound that decreases the enzymatic activity of the polypeptide is thereby identified as a potential therapeutic agent for decreasing the enzymatic activity of the human transmembrane serine protease.

Still another embodiment of the invention is a method of screening for therapeutic agents that can regulate an activity of a human transmembrane serine protease. A test compound is contacted with a product encoded by a polynucleotide comprising a nucleotide sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof. Binding of the test compound to the product is detected. A test compound that binds to the product is thereby identified as a potential therapeutic agent for regulating the activity of the human transmembrane serine protease.

Another embodiment of the invention is a method of reducing an activity of a human transmembrane serine protease. A cell comprising the human transmembrane serine protease is contacted with a reagent that specifically binds to a product encoded by a polynucleotide comprising a nucleotide sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof. The activity of the human transmembrane serine protease is thereby reduced.

Yet another embodiment of the invention is a pharmaceutical composition, comprising a reagent and a pharmaceutically acceptable carrier. The reagent specifically binds to a polypeptide comprising an amino acid sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof; and Even another embodiment of the invention is a pharmaceutical composition comprising a reagent and a pharmaceutically acceptable carrier. The reagent specifically binds to a product of a polynucleotide comprising a coding sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof.

A further embodiment of the invention is a pharmaceutical composition comprising an expression vector and a pharmaceutically acceptable carrier. The expression vector encodes a polypeptide comprising an amino acid sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof.

Still another embodiment of the invention is a method of treating a disorder selected from the group consisting of chronic obstructive pulmonary disease, cancer, metastasis of malignant cells, tumor angiogenesis, inflammation, atherosclerosis, neurodegenerative diseases, and pathogenic infections. A therapeutically effective dose of a reagent that inhibits a function of a human transmembrane some protease is administered to a patient in need thereof. The human transmembrane serine protease comprises an amino acid sequence selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof. Symptoms of the disorder are thereby ameliorated.

Even another embodiment of the invention is a isolated polynucleotide selected from the group consisting of: (a) a polynucleotide encoding a protein that comprises the amino acid sequence of SEQ ID NO:12, (b) a polynucleotide comprising the sequence of SEQ ID NO:11, (c) a polynucleotide comprising a coding sequence of a cDNA contained within plasmid pCRII-TMSP3 (ATCC Accession No. PTA-3433), (d) a polynucleotide encoding a protein that comprises the amino acid sequence encoded by the cDNA of plasmid pCRII-TMSP3, (e) a polynucleotide which hybridizes under stringent conditions to a polynucleotide specified in (a)–(d); (e) a polynucleotide having a nucleic acid sequence that deviates from the nucleic acid sequences specified in (a)–(d) due to the degeneration of the genetic code, and (f) a polynucleotide that represents a fragment, derivative, or allelic variation of a nucleic acid sequence specified in (a)–(c).

Yet another embodiment of the invention is an expression vector comprising polynucleotide selected from the group consisting of: (a) a polynucleotide encoding a protein that comprises the amino acid sequence of SEQ ID NO:12, (b) a polynucleotide comprising the sequence of SEQ ID NO:11, (c) a polynucleotide comprising a coding sequence of a cDNA contained within plasmid pCRII-TMSP3 (ATCC Accession No. PTA-3433), (d) a polynucleotide encoding a protein that comprises the amino acid sequence encoded by the cDNA of plasmid pCRII-TMSP3, (e) a polynucleotide which hybridizes under stringent conditions to a polynucleotide specified in (a)–(d); (e) a polynucleotide having a nucleic acid sequence that deviates from the nucleic acid sequences specified in (a)–(d) due to the degeneration of the genetic code, and (f) a polynucleotide that represents a fragment, derivative, or allelic variation of a nucleic acid sequence specified in (a)–(e).

A further embodiment of the invention is a host cell comprising an expression vector comprising polynucleotide selected from the group consisting of: (a) a polynucleotide encoding a protein that comprises the amino acid sequence of SEQ ID NO:12, (b) a polynucleotide comprising the sequence of SEQ ID NO:11, (c) a polynucleotide comprising a coding sequence of a cDNA contained within plasmid pCRII-TMSP3 (ATCC Accession No. PTA-3433), (d) a polynucleotide encoding a protein that comprises the amino acid sequence encoded by the cDNA of plasmid pCRII-TMSP3, (e) a polynucleotide which hybridizes under stringent conditions to a polynucleotide specified in (a)–(d); (e) a polynucleotide having a nucleic acid sequence that deviates from the nucleic acid sequences specified in (a)–(d) due to the degeneration of the genetic code, and (f) a polynucleotide that represents a fragment, derivative, or allelic variation of a nucleic acid sequence specified in (a)–(e).

Another embodiment of the invention is a preparation of antibodies that specifically bind to a polypeptide selected from the group consisting of (a) the amino acid sequence shown in SEQ ID NO:12, (b) the amino acid sequence encoded by a cDNA insert contained within plasmid pCRII-TMSP3 (ATCC Accession No. PTA-3433), and (c) biologically active variants thereof.

Even another embodiment of the invention is a antisense oligonucleotide that hybridizes to a polynucleotide selected from the group consisting of (a) a polynucleotide encoding a protein that comprises the amino acid sequence of SEQ ID NO:12, (b) a polynucleotide comprising the sequence of SEQ ID NO:11, (c) a polynucleotide comprising a coding sequence of a cDNA contained within plasmid pCRII-TMSP3 (ATCC Accession No. PTA-3433), (d) a polynucleotide encoding a protein that comprises the amino acid sequence encoded by the cDNA of plasmid pCRII-TMSP3, (e) a polynucleotide which hybridizes under stringent conditions to a polynucleotide specified in (a)–(d); (e) a polynucleotide having a nucleic acid sequence that deviates from the nucleic acid sequences specified in (a)–(d) due to the degeneration of the genetic code, and (t) a polynucleotide that represents a fragment, derivative, or allelic variation of a nucleic acid sequence specified in (a)–(e).

The invention thus provides reagents and methods for regulating human transmembrane serine protease activity, which can be used inter alia, to treat COPD, metastasis of malignant cells, tumor angiogenesis, inflammation, atherosclerosis, neurodegenerative diseases, and pathogenic infections.

BRIEF DESCRIPTION OF THE DRAWINGS

FIG. 1. Alignment of human transmembrane serine protease as shown in SEQ ID NO:12 with the protein identified by SwissProt Accession No. O15393 (SEQ ID NO:14).

FIG. 2. Prosite search results.

FIG. 3. BLOCKS search results.

FIG. 4. Relative expression of human transmembrane serine protease in respiratory cells and tissues.

DETAILED DESCRIPTION OF THE INVENTION

Figure 5:
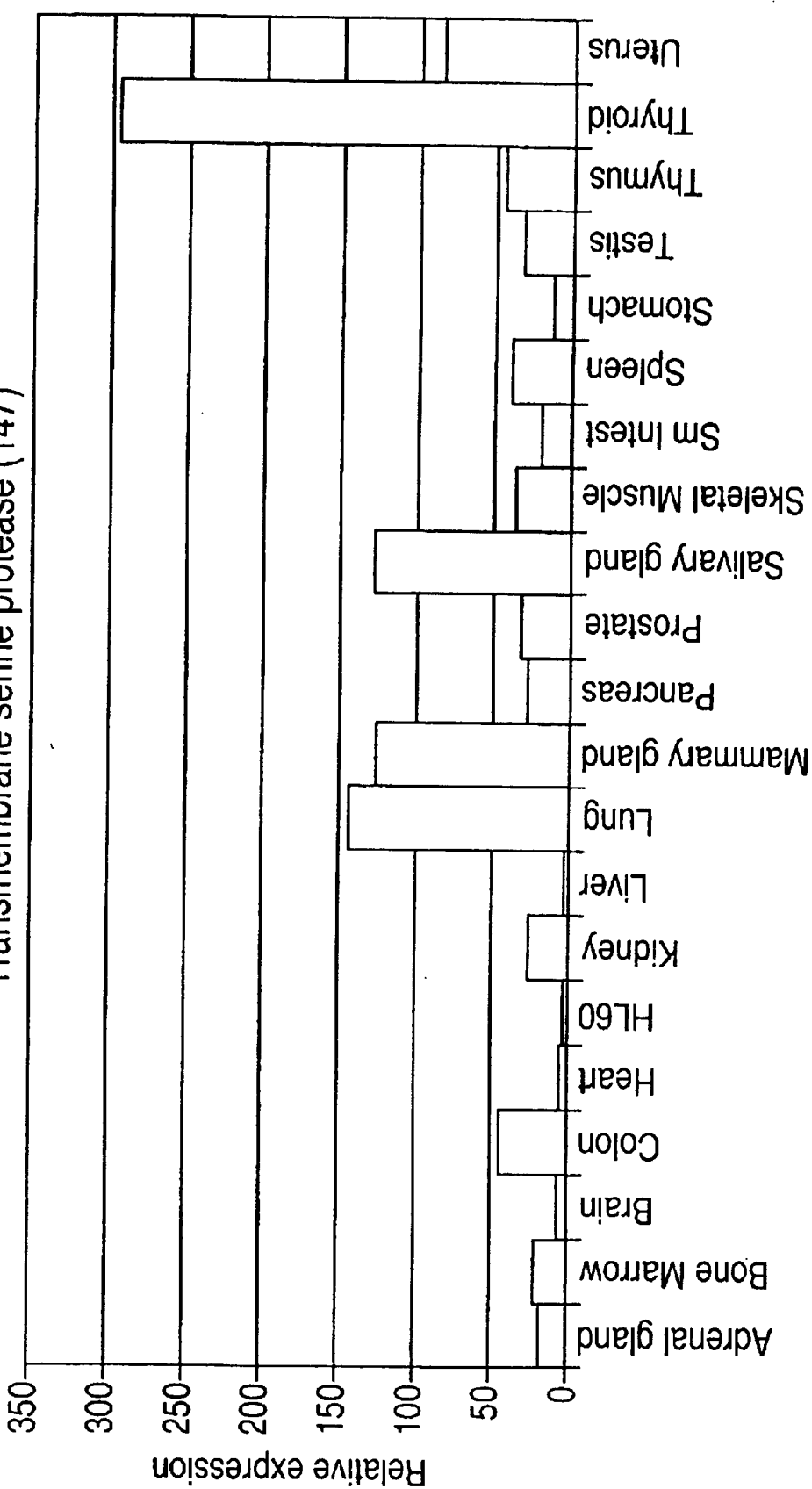
FIG. 5. Relative expression of human transmembrane serine protease in various human tissues and the neutrophil-like cell line HL60.

It is a discovery of the present invention that regulators of a human transmembrane serine protease can be used to regulate degradation of the extracellular matrix. Human transmembrane serine protease as shown in SEQ ID NO:12 is 38% identical over a 370 amino acid overlap to the protein identified by SwissProt Accession No. O15393 (SEQ ID NO:14) and annotated as a transmembrane serine protease 2 (FIG. 1). Related ESTs (SEQ ID NOS:1–8) are expressed in placenta, breast, colon, and ovarian tumor. The results of Prosite and BLOCKS searches are shown in FIGS. 2 and 3, respectively. Human transmembrane serine protease is therefore expected to be useful for the same purposes as previously identified serine proteases.

Polypeptides

Transmembrane serine protease polypeptides according to the invention comprise at least 10, 15, 25, 50, 75, 100, 125, 150, 175, 200, 225, 250, 275, 300, 350, 400, or 410 contiguous amino acids selected from SEQ ID NO:12 or from a biologically active variant thereof, as defined below. A transmembrane serine protease polypeptide of the invention therefore can be a portion of a transmembrane serine protease molecule, a full-length transmembrane serine protease molecule, or a fusion protein comprising all or a portion of a transmembrane serine protease molecule.

Biologically Active Variants

Transmembrane serine protease variants that are biologically active, i.e., retain a transmembrane serine protease activity, also are transmembrane serine protease polypeptides. Preferably, naturally or non-naturally occurring transmembrane serine protease variants have amino acid sequences which are at least about 50, preferably about 75, 90, 96, or 98% identical to an amino acid sequence shown in SEQ ID NO:12. Percent identity between a putative transmembrane serine protease variant and an amino acid sequence of SEQ ID NO:12 is determined using the Blast2 alignment program (Blosum62, Expect 10, standard genetic codes).

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 2 to 5 amino acids. Guidance in determining which amino acid residues can be substituted, inserted, or deleted without abolishing biological or immunological activity can be found using computer programs well known in the art, such as DNASTAR software. Whether an amino acid change results in a biologically active transmembrane serine protease polypeptide can readily be determined by assaying for fibronectin binding or for transmembrane serine protease activity, as is known in the art and described, for example, in Example 2.

Fusion Proteins

Fusion proteins are useful for generating antibodies against transmembrane serine protease amino acid sequences and for use in various assay systems. For example, fusion proteins can be used to identify proteins that interact with portions of a transmembrane serine protease polypeptide, including its active site and fibronectin domains. Methods such as protein affinity chromatography or library-based assays for protein-protein interactions, such as the yeast two-hybrid or phage display systems, can be used for this purpose. Such methods are well known in the art and also can be used as drug screens.

A transmembrane serine protease fusion protein comprises two protein segments fused together by means of a peptide bond. For example, the first protein segment can comprise at least 10, 15, 25, 50, 75, 100, 125, 150, 175, 200, 225, 250, 275, 300, 350, 400, or 410 contiguous amino acids selected from SEQ ID NO:12 or a biologically active variant thereof. Preferably, a fusion protein comprises the active site of the protease, one or both of the trypsin_ser or trypsin_ his domains, or one or more of the functional domains identified in FIGS. 1–3. The first protein segment also can comprise full-length transmembrane serine protease.

The second protein segment can be a full-length protein or a protein fragment or polypeptide. Proteins commonly used in fusion protein construction include β-galactosidase, β-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GAL4 DNA binding domain fusions, and herpes simplex virus (HSV) BP16 protein fusions. A fusion protein also can be engineered to contain a cleavage site located between the transmembrane serine protease polypeptide-encoding sequence and the heterologous protein sequence, so that the transmembrane serine protease polypeptide can be cleaved and purified away from the heterologous moiety.

A fusion protein can be synthesized chemically, as is known in the art. Preferably, a fusion protein is produced by covalently linking two protein segments or by standard procedures in the art of molecular biology. Recombinant DNA methods can be used to prepare fusion proteins, for example, by making a DNA construct which comprises transmembrane serine protease coding sequences disclosed herein in proper reading frame with nucleotides encoding the second protein segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human transmembrane serine protease can be obtained using transmembrane serine protease polynucleotides (described below) to make suitable probes or primers to screening cDNA expression libraries from other species, such as mice, monkeys, or yeast, identifying cDNAs which encode homologs of transmembrane serine protease, and expressing the cDNAs as is known in the art.

Polynucleotides

A transmembrane serine protease polynucleotide can be single- or double-stranded and comprises a coding sequence or the complement of a coding sequence for a transmembrane serine protease polypeptide. A coding sequence for the transmembrane serine protease of SEQ ID NO:12 is shown in SEQ ID NO:11.

Degenerate nucleotide sequences encoding human transmembrane serine protease polypeptides, as well as homologous nucleotide sequences which are at least about 50, 55, 60, 65, 70, preferably about 75, 90, 96, or 98% identical to the transmembrane serine protease coding sequence shown in SEQ ID NO:11 also are transmembrane serine protease polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of transmembrane serine protease polynucleotides that encode biologically active transmembrane serine protease polypeptides also are transmembrane serine protease polynucleotides.

Identification of Variants and Homologs

Variants and homologs of the transmembrane serine protease polynucleotides disclosed above also are transmembrane serine protease polynucleotides. Typically, homologous transmembrane serine protease polynucleotide sequences can be identified by hybridization of candidate polynucleotides to known transmembrane serine protease polynucleotides under stringent conditions, as is known in the art. For example, using the following wash conditions— 2X SSC (0.3 M NaCl, 0.03 M sodium citrate, pH 7.0), 0.1% SDS, room temperature twice, 30 minutes each; then 2X SSC, 0.1% SDS, 50° C. once, 30 minutes; then 2X SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the transmembrane serine protease polynucleotides disclosed herein can be identified by making suitable probes or primers and screening cDNA expression libraries from other species, such as mice, monkeys, or yeast. Human variants of transmembrane serine protease polynucleotides can be identified, for example, by screening human cDNA expression libraries. It is well known that the $T_m$ of a double-stranded DNA decreases by 1–1.5° C. with every 1% decrease in homology (Bonner et al., *J. Mol Biol* 81, 123 (1973). Variants of human transmembrane serine protease polynucleotides or transmembrane serine protease polynucleotides of other species can therefore be identified, for example, by hybridizing a putative homologous transmembrane serine protease polynucleotide with a polynucleotide having a nucleotide sequence of SEQ ID NO:11 to form a test hybrid. The melting temperature of the test hybrid is compared with the melting temperature of a hybrid comprising transmembrane serine protease polynucleotides having perfectly complementary nucleotide sequences, and the number or percent of basepair mismatches within the test hybrid is calculated.

Nucleotide sequences which hybridize to transmembrane serine protease polynucleotides or their complements following stringent hybridization and/or wash conditions are also transmembrane serine protease polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between a transmembrane serine protease polynucleotide having a coding sequence disclosed herein and a polynucleotide sequence which is at least about 50, 55, 60, 65, 70, preferably about 75, 90, 96, or 98% identical to that nucleotide sequence can be calculated, for example, using the equation of Bolton and McCarthy, Proc. Natl. Acad. Sci. U.S.A. 48, 1390 (1962):

$$T_m = 81.5° C. - 16.6(\log_{10}[Na^+]) + 0.41(\%G+C) - 0.63(\%formamide) - 600/l),$$

where l=the length of the hybrid in basepairs.
Stringent wash conditions include, for example, 4X SSC at 65° C., or 50% formamide, 4X SSC at 42° C., or 0.5X SSC, 0.1% SDS at 65° C. Highly stringent wash conditions include, for example, 0.2X SSC at 65° C.

Preparation of Polynucleotides

A naturally occurring transmembrane serine protease polynucleotide can be isolated free of other cellular components such as membrane components, proteins, and lipids. Polynucleotides can be made by a cell and isolated using standard nucleic acid purification techniques, synthesized using an amplification technique, such as the polymerase chain reaction (PCR), or synthesized using an automatic synthesizer. Methods for isolating polynucleotides are routine and are known in the art. Any such technique for obtaining a polynucleotide can be used to obtain isolated transmembrane serine protease polynucleotides. For example, restriction enzymes and probes can be used to isolate polynucleotide fragments that comprise transmembrane serine protease nucleotide sequences. Isolated polynucleotides are in preparations that are free or at least 70, 80, or 90% free of other molecules.

Transmembrane serine protease cDNA molecules can be made with standard molecular biology techniques, using transmembrane serine protease mRNA as a template. Transmembrane serine protease cDNA molecules can thereafter be replicated using molecular biology techniques known in the art and disclosed in manuals such as Sambrook et al. (1989). An amplification technique, such as PCR, can be used to obtain additional copies of transmembrane serine protease polynucleotides, using either human genomic DNA or cDNA as a template.

Alternatively, synthetic chemistry techniques can be used to synthesize transmembrane serine protease polynucleotides. The degeneracy of the genetic code allows alternate nucleotide sequences to be synthesized which will encode a transmembrane serine protease polypeptide having, for example, the amino acid sequence shown in SEQ ID NO:12 or a biologically active variant of that sequence.

Extending Polynucleotides

Various PCR-based methods can be used to extend the nucleic acid sequences encoding the disclosed portions of human transmembrane serine protease to detect upstream sequences such as promoters and regulatory elements. For example, restriction-site PCR uses universal primers to retrieve unknown sequence adjacent to a known locus (Sarkar, PCR Methods Applic. 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., Nucleic Acids Res. 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., PCR Methods Applic. 1, 111–119, 1991). In this method, multiple restriction enzyme digestions and ligations are used to place an engineered double-stranded sequence into an unknown fragment of the DNA molecule before performing PCR.

Another method that can be used to retrieve unknown sequences is that of Parker et al., Nucleic Acids Res. 19, 3055–3060, 1991. Additionally, PCR, nested primers, and PROMOTERFINDER libraries (CLONTECH, Palo Alto, Calif.) can be used to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences that contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) which are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA that might be present in limited amounts in a particular sample.

Obtaining Polypeptides

Transmembrane serine protease polypeptides can be obtained, for example, by purification from cells, by expression of transmembrane serine protease polynucleotides, or by direct chemical synthesis.

Protein Purification

Transmembrane serine protease polypeptides can be purified from cells, such as primary tumor cells, metastatic cells, or cancer cell lines (e.g., colon cancer cell lines HCT116, DLD1, HT29, Caco2, SW837, SW480, and RKO, breast cancer cell lines 21-PT, 21-MT, MDA-468, SK-BR3, and BT-474, the A549 lung cancer cell line, or the H392 glioblastoma cell line), as well as cells transfected with a transmembrane serine protease expression construct. Placenta, breast, colon, and ovarian tumor are especially useful sources of transmembrane serine protease polypeptides. A purified transmembrane serine protease polypeptide is separated from other compounds that normally associate with the transmembrane serine protease polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified transmembrane serine protease polypeptides is at least 80% pure; preferably, the preparations are 90%, 95%, or 99% pure. Purity of the preparations can be assessed by any means known in the art, such as SDS-polyacrylamide gel electrophoresis. Enzymatic activity of the purified preparations can be assayed, for example, as described in Example 2.

Expression of Polynucleotides

To express a transmembrane serine protease polypeptide, a transmembrane serine protease polynucleotide can be inserted into an expression vector which contains the necessary elements for the transcription and translation of the inserted coding sequence. Methods that are well known to those skilled in the art can be used to construct expression vectors containing sequences encoding transmembrane serine protease polypeptides and appropriate transcriptional and translational control elements. These methods include in vitro recombinant DNA techniques, synthetic techniques, and in vivo genetic recombination. Such techniques are described, for example, in Sambrook et al. (1989) and Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a transmembrane serine protease polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage protein genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a transmembrane serine protease polypeptide, vectors based on SV40 or EBV can be used with an appropriate selectable marker.

Bacterial and Yeast Expression Systems

In bacterial systems, a number of expression vectors can be selected depending upon the use intended for the transmembrane serine protease polypeptide. For example, when a large quantity of a transmembrane serine protease polypeptide is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene), in which the sequence encoding the transmembrane serine protease polypeptide can be ligated into the vector in frame with sequences for the amino-terminal Met and the subsequent 7 residues of β-galactosidase so that a hybrid protein is produced. pIN vectors (Van Heeke & Schuster, *J. Biol Chem.* 264, 5503–5509, 1989 or pGEX vectors (Promega, Madison, Wis.) can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or Factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516–544, 1987.

Plant and Insect Expression Systems

If plant expression vectors are used, the expression of sequences encoding transmembrane serine protease polypeptides can be driven by any of a number of promoters. For example, viral promoters such as the 35S and 19S promoters of CaMV can be used alone or in combination with the omega leader sequence from TMV (Takamatsu *EMBO J.* 6, 307–311, 1987). Alternatively, plant promoters such as the small subunit of RUBISCO or heat shock promoters can be used (Coruzzi et al., *EMBO J.* 3, 1671–1680, 1984; Broglie et al., *Science* 224, 838–843, 1984; Winter et al., *Results Probl. Cell Differ.* 17, 85–105, 1991). These constructs can be introduced into plant cells by direct DNA transformation or by pathogen-mediated transfection. Such techniques are described in a number of generally available reviews (see, for example, Hobbs or Murray, in McGRAW HILL YEARBOOK OF SCIENCE AND TECHNOLOGY, McGraw Hill, New York, N.Y., pp. 191–196, 1992).

An insect system also can be used to express a transmembrane serine protease polypeptide. For example, in one such system *Autographa californica* nuclear polyhedrosis virus (AcNPV) is used as a vector to express foreign genes in *Spodoptera frugiperda* cells or in *Trichoplusia larvae*. Sequences encoding transmembrane serine protease polypeptides can be cloned into a non-essential region of the virus, such as the polyhedrin gene, and placed under control of the polyhedrin promoter. Successful insertion of transmembrane serine protease polypeptides will render the polyhedrin gene inactive and produce recombinant virus lacking coat protein. The recombinant viruses can then be used to infect, for example, *S. frugiperda* cells or *Trichoplusia larvae* in which transmembrane serine protease polypeptides can be expressed (Engelhard et al., *Proc. Nat. Acad. Sci.* 91, 3224–3227, 1994).

Mammalian Expression Systems

A number of viral-based expression systems can be utilized in mammalian host cells. For example, if an adenovirus is used as an expression vector, sequences encoding transmembrane serine protease polypeptides can be ligated into an adenovirus transcription/translation complex consisting of the late promoter and tripartite leader sequence. Insertion in a non-essential E1 or E3 region of the viral genome can be used to obtain a viable virus which is capable of expressing a transmembrane serine protease polypeptide in infected host cells (Logan & Shenk, *Proc. Natl. Acad. Sci.* 81, 3655–3659, 1984). In addition, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding transmembrane serine protease polypeptides. Such signals include the ATG initiation codon and adjacent sequences. In cases where sequences encoding a transmembrane serine protease polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers that are appropriate for the particular cell system that is used (see Scharf et al., *Results Probl. Cell Differ.* 20, 125–162, 1994).

Host Cells

A host cell strain can be chosen for its ability to modulate the expression of the inserted sequences or to process an expressed transmembrane serine protease polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells that have specific cellular machinery and characteristic mechanisms for post-translational activities (e.g., CHO, HeLa, MDCK, HEK293, and W138), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines that stably express transmembrane serine protease polypeptides can be transformed using expression vectors that can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells that successfully express the introduced transmembrane serine protease sequences. Resistant clones of stably transformed cells can be proliferated using tissue culture techniques appropriate to the cell type.

Any number of selection systems can be used to recover transformed cell lines. These include, but are not limited to, the herpes simplex virus thymidine kinase (Wigler et al., *Cell* 11, 223-32, 1977) and adenine phosphoribosyltransferase (Lowy et al., *Cell* 22, 817-23, 1980). Genes that can be employed in $tk^-$ or $aprt^-$ cells, respectively. Also, antimetabolite, antibiotic, or herbicide resistance can be used as the basis for selection. For example, dhfr confers resistance to methotrexate (Wigler et al., *Proc. Natl. Acad. Sci.* 77, 3567-70, 1980); npt confers resistance to the aminoglycosides, neomycin and G-418 (Colbere-Garapin et al., *J. Mol. Biol.* 150, 1–14, 1981); and als and pat confer resistance to chlorsulfuron and phosphinotricin acetyltransferase, respectively (Murray, 1992 supra). Additional selectable genes have been described, for example trpB, which allows cells to utilize indole in place of tryptophan, or hisD, which allows cells to utilize histinol in place of histidine (Hartman & Mulligan, *Proc. Natl. Acad. Sci.* 85, 8047-51, 1988). Visible markers such as anthocyanins, -glucuronidase and its substrate GUS, and luciferase and its substrate luciferin, can be used to identify transformants and to quantify the amount of transient or stable protein expression attributable to a specific vector system (Rhodes et al., *Methods Mol. Biol.* 55, 121–131, 1995).

Detecting Expression of Polypeptides

Although the presence of marker gene expression suggests that the transmembrane serine protease polynucleotide is also present, its presence and expression may need to be confirmed. For example, if a sequence encoding a transmembrane serine protease polypeptide is inserted within a marker gene sequence, transformed cells containing sequences that encode a transmembrane serine protease polypeptide can be identified by the absence of marker gene function. Alternatively, a marker gene can be placed in tandem with a sequence encoding a transmembrane serine protease polypeptide under the control of a single promoter. Expression of the marker gene in response to induction or selection usually indicates expression of the transmembrane serine protease polynucleotide.

Alternatively, host cells which contain a transmembrane serine protease polynucleotide and which express a transmembrane serine protease polypeptide can be identified by a variety of procedures known to those of skill in the art. These procedures include, but are not limited to, DNA-DNA or DNA-RNA hybridizations and protein bioassay or immunoassay techniques that include membrane, solution, or chip-based technologies for the detection and/or quantification of nucleic acid or protein.

The presence of a polynucleotide sequence encoding a transmembrane serine protease polypeptide can be detected by DNA-DNA or DNA-RNA hybridization or amplification using probes or fragments or fragments of polynucleotides encoding a transmembrane serine protease polypeptide. Nucleic acid amplification-based assays involve the use of oligonucleotides selected from sequences encoding a transmembrane serine protease polypeptide to detect transformants that contain a transmembrane serine protease polynucleotide.

A variety of protocols for detecting and measuring the expression of a transmembrane serine protease polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a transmembrane serine protease polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., J. Exp. Med. 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding transmembrane serine protease polypeptides include oligolabeling, nick translation, end-labeling, or PCR amplification using a labeled nucleotide. Alternatively, sequences encoding a transmembrane serine protease polypeptide can be cloned into a vector for the production of an mRNA probe. Such vectors are known in the art, are commercially available, and can be used to synthesize RNA probes in vitro by addition of labeled nucleotides and an appropriate RNA polymerase, such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, fluorescent, chemiluminescent, or chromogenic agents, as well as substrates, cofactors, inhibitors, magnetic particles, and the like.

Expression and Purification of Polypeptides

Host cells transformed with nucleotide sequences encoding a transmembrane serine protease polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides that encode transmembrane serine protease polypeptides can be designed to contain signal sequences that direct secretion of transmembrane serine protease polypeptides through a prokaryotic or eukaryotic cell membrane.

Other constructions can be used to join a sequence encoding a transmembrane serine protease polypeptide to a nucleotide sequence encoding a polypeptide domain that will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor Xa or enterokinase (Invitrogen, San Diego, Calif.) between the purification domain and the transmembrane serine protease polypeptide can be used to facilitate purification. One such expression vector provides for expression of a fusion protein containing a transmembrane serine protease polypeptide and 6 histidine residues preceding a thioredoxin or an enterokinase cleavage site. The histidine residues facilitate purification on IMAC (immobilized metal ion affinity chromatography as described in Porath et al., Prot. Exp. Purif. 3, 263–281, 1992), while the enterokinase cleavage site provides a means for purifying the transmembrane serine protease polypeptide from the fusion protein. Vectors which contain fusion proteins are disclosed in Kroll et al., DNA Cell Biol. 12, 441–453, 1993).

Chemical Synthesis

Sequences encoding a transmembrane serine protease polypeptide can be synthesized, in whole or in part, using chemical methods well known in the art (see Caruthers et al., Nucl. Acids Res. Symp. Ser. 215–223, 1980; Horn et al. Nucl. Acids Res. Symp. Ser. 225–232, 1980). Alternatively, a transmembrane serine protease polypeptide itself can be produced using chemical methods to synthesize its amino acid sequence. For example, transmembrane serine protease polypeptides can be produced by direct peptide synthesis using solid-phase techniques (Merrifield, J. Am. Chem. Soc. 85, 2149–2154, 1963; Roberge et al., Science 269, 202–204, 1995). Protein synthesis can be performed using manual techniques or by automation. Automated synthesis can be achieved, for example, using Applied Biosystems 431A Peptide Synthesizer (Perkin Elmer). Various fragments of transmembrane serine protease polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, WH Freeman and Co., New York, N.Y., 1983). The composition of a synthetic transmembrane serine protease polypeptide can be confirmed by amino acid analysis or sequencing (e.g., the Edman degradation procedure; see Creighton, supra). Additionally, any portion of the amino acid sequence of the transmembrane serine protease polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce transmembrane serine protease polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life that is longer than that of a transcript generated from the naturally occurring sequence.

The nucleotide sequences disclosed herein can be engineered using methods generally known in the art to alter transmembrane serine protease polypeptide-encoding sequences for a variety of reasons, including modification of the cloning, processing, and/or expression of the gene product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of a transmembrane serine protease polypeptide. "Antibody" as used herein includes intact immunoglobulin molecules, as well as fragments thereof, such as Fab, F(ab$^1$)$_2$, and Fv, which are capable of binding an epitope of a transmembrane serine protease polypeptide. Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a transmembrane serine protease polypeptide can be used therapeutically, as well as in immunochemical assays, including but not limited to Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody that specifically binds to the immunogen.

Typically, an antibody that specifically binds to a transmembrane serine protease polypeptide provides a detection signal at least 5-, 10-, or 20-fold higher than a detection signal provided with other proteins when used in an immunochemical assay. Preferably, antibodies that specifically bind to transmembrane serine protease polypeptides do not detect other proteins in immunochemical assays and can immunoprecipitate a transmembrane serine protease polypeptide from solution.

Transmembrane serine protease polypeptides can be used to immunize a mammal, such as a mouse, rat, rabbit, guinea pig, monkey, or human, to produce polyclonal antibodies. If desired, a transmembrane serine protease polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (*bacilli Calmette-Guerin*) and *Corynebacterium parvum* are especially useful.

Monoclonal antibodies that specifically bind to a transmembrane serine protease polypeptide can be prepared using any technique that provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495–497, 1985; Kozbor et al., *J. Immunol. Methods* 81, 31–42, 1985; Cote et al., *Proc. Natl. Acad. Sci.* 80, 2026–2030, 1983; Cole et al., *Mol. Cell Biol* 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc. Natl. Acad. Sci.* 81, 6851–6855, 1984; Neuberger et al., *Nature* 312, 604–608, 1984; Takeda et al., *Nature* 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, one can produce humanized antibodies using recombinant methods, as described in GB2188638B. Antibodies that specifically bind to a transmembrane serine protease polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies that specifically bind to transmembrane serine protease polypeptides. Antibodies with related specificity, but of distinct idiotypic composition, can be generated by chain shuffling from random combinatorial immunoglobin libraries (Burton, *Proc. Natl. Acad. Sci.* 88, 11120-23, 1991).

Single-chain antibodies also can be constructed using a DNA amplification method, such as PCR, using hybridoma cDNA as a template (Thirion et al., 1996, *Eur. J. Cancer Prev.* 5, 507-11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159-63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology. Verhaar et al., 1995, *Int. J. Cancer* 61, 497–501; Nicholls et al., 1993, *J. Immunol. Meth.* 165, 81–91.

Antibodies which specifically bind to transmembrane serine protease polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies of the invention can be purified by methods well known in the art. For example, antibodies can be affinity purified by passage over a column to which a transmembrane serine protease polypeptide is bound. The bound antibodies can then be eluted from the column using a buffer with a high salt concentration.

Antisense Oligonucleotides

Antisense oligonucleotides are nucleotide sequences that are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of transmembrane serine protease gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, Meth. Mol. Biol. 20, 1–8, 1994; Sonveaux, Meth. Mol. Biol. 26, 1–72, 1994; Uhlmann et al., Chem. Rev. 90, 543–583, 1990.

Modifications of transmembrane serine protease gene expression can be obtained by designing antisense oligonucleotides that will form duplexes to the control, 5', or regulatory regions of the transmembrane serine protease gene. Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful duplex formation between an antisense oligonucleotide and the complementary sequence of a transmembrane serine protease polynucleotide. Antisense oligonucleotides which comprise, for example, 2, 3, 4, or 5 or more stretches of contiguous nucleotides which are precisely complementary to a transmembrane serine protease polynucleotide, each separated by a stretch of contiguous nucleotides which are not complementary to adjacent transmembrane serine protease nucleotides, can provide targeting specificity for transmembrane serine protease mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular transmembrane serine protease polynucleotide sequence.

Antisense oligonucleotides can be modified without affecting their ability to hybridize to a transmembrane serine protease polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3', 5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., Trends Biotechnol. 10, 152–158, 1992; Uhlmann et al., Chem. Rev. 90, 543–584, 1990; Uhlmann et al., Tetrahedron. Lett. 215, 3539–3542, 1987.

Ribozymes

Ribozymes are RNA molecules with catalytic activity. See, e.g., Cech, Science 236, 1532–1539; 1987; Cech, Ann. Rev. Biochem. 59, 543–568; 1990, Cech, Curr. Opin. Struct. Biol. 2, 605–609; 1992, Couture & Stinchcomb, Trends Genet. 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of a transmembrane serine protease polynucleotide can be used to generate ribozymes which will specifically bind to mRNA transcribed from the transmembrane serine protease polynucleotide. Methods of designing and constructing ribozymes which can cleave other RNA molecules in trans in a highly sequence specific manner have been developed and described in the art (see Haseloff et al. Nature 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a transmembrane serine protease RNA target are initially identified by scanning the RNA molecule for ribozyme cleavage sites which include the following sequences: GUA, GUU, and GUC. Once identified, short RNA sequences of between 15 and 20 ribonucleotides corresponding to the region of the transmembrane serine protease target RNA containing the cleavage site can be evaluated for secondary structural features which may render the target inoperable. The suitability of candidate targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related; thus, upon hybridizing to the transmembrane serine protease target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease transmembrane serine protease expression. Alternatively, if it is desired that the cells stably retain the DNA construct, it can be supplied on a plasmid and maintained as a separate element or integrated into the genome of the cells, as is known in the art. The DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors that induce expression of a target gene. Ribozymes also can be engineered to provide an additional level of regulation, so that destruction of transmembrane serine protease mRNA occurs only when both a ribozyme and a target gene are induced in the cells.

Differentially Expressed Genes

Described herein are methods for the identification of genes whose products interact with human transmembrane serine protease. Such genes may represent genes that are differentially expressed in disorders including, but not limited to, COPD, CNS disorders, cardiovascular disorders, and cancer. Further, such genes may represent genes that are differentially regulated in response to manipulations relevant to the progression or treatment of such diseases. Additionally, such genes may have a temporally modulated expression, increased or decreased at different stages of tissue or organism development. A differentially expressed gene may also have its expression modulated under control versus experimental conditions. In addition, the human transmembrane serine protease gene or gene product may itself be tested for differential expression.

The degree to which expression differs in a normal versus a diseased state need only be large enough to be visualized via standard characterization techniques such as differential display techniques. Other such standard characterization techniques by which expression differences may be visualized include but are not limited to, quantitative RT (reverse transcriptase), PCR, and Northern analysis.

Identification of Differentially Expressed Genes

To identify differentially expressed genes total RNA or, preferably, mRNA is isolated from tissues of interest. For example, RNA samples are obtained from tissues of experimental subjects and from corresponding tissues of control subjects. Any RNA isolation technique that does not select against the isolation of mRNA may be utilized for the purification of such RNA samples. See, for example, Ausubel et al., ed., CURRENT PROTOCOLS IN MOLECULAR BIOLOGY, John Wiley & Sons, Inc. New York, 1987–1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples that represent RNA produced by differentially expressed genes are identified by methods well known to those of skill in the art. They include, for example, differential screening (Tedder et al., Proc. Natl. Acad. Sci. U.S.A. 85, 208-12, 1988), subtractive hybridization (Hedrick et al., Nature 308, 149-53; Lee et al., Proc. Natl. Acad. Sci. U.S.A. 88, 2825, 1984), and differential display (Liang & Pardee, Science 257, 967-71, 1992; U.S. Pat. No. 5,262,311), and microarrays.

The differential expression information may itself suggest relevant methods for the treatment of disorders involving the human transmembrane serine protease. For example, treatment may include a modulation of expression of the differentially expressed genes and/or the gene encoding the human transmembrane serine protease. The differential expression information may indicate whether the expression or activity of the differentially expressed gene or gene product or the human transmembrane serine protease gene or gene product are up-regulated or down-regulated.

Screening Methods

The invention provides methods for identifying modulators, i.e., candidate or test compounds which bind to transmembrane serine protease polypeptides or polynucleotides and/or have a stimulatory or inhibitory effect on, for example, expression or activity of the transmembrane serine protease polypeptide or polynucleotide, so as to regulate degradation of the extracellular matrix. Decreased extracellular matrix degradation is useful for preventing or suppressing malignant cells from metastasizing. Increased extracellular matrix degradation may be desired, for example, in developmental disorders characterized by inappropriately low levels of extracellular matrix degradation or in regeneration.

The invention provides assays for screening test compounds that bind to or modulate the activity of a transmembrane serine protease polypeptide or a transmembrane serine protease polynucleotide. A test compound preferably binds to a transmembrane serine protease polypeptide or polynucleotide. More preferably, a test compound decreases a transmembrane serine protease activity of a transmembrane serine protease polypeptide or expression of a transmembrane serine protease polynucleotide by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, Anticancer Drug Des. 12, 145, 1997.

Methods for the synthesis of molecular libraries are well known in the art (see, for example, DeWitt et al., Proc. Natl. Acad. Sci. U.S.A. 90, 6909, 1993; Erb et al. Proc. Natl. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994). Libraries of compounds can be presented in solution (see, e.g., Houghten, Bio Techniques 13, 412–421, 1992), or on beads (Lam, Nature 354, 82–84, 1991), chips (Fodor, Nature 364, 555–556, 1993), bacteria or spores (Ladner, U.S. Pat. No. 5,223,409), plasmids (Cull et al., Proc. Natl. Acad. Sci. U.S.A. 89, 1865–1869, 1992), or:phage (Scott & Smith, Science 249, 386–390, 1990; Devlin, Science 249, 404–406, 1990); Cwirla et al., Proc. Natl. Acad. Sci. 97, 6378–6382, 1990; Felici, J. Mol. Biol. 222, 301–310, 1991; and Ladner, U.S. Pat. No. 5,223,409).

High Throughput Screening

Test compounds can be screened for the ability to bind to transmembrane serine protease polypeptides or polynucleotides or to affect transmembrane serine protease activity or transmembrane serine protease gene expression using high throughput screening. Using high throughput screening, many discrete compounds can be tested in parallel so that large numbers of test compounds can be quickly screened. The most widely established techniques utilize 96-well microtiter plates. The wells of the microtiter plates typically require assay volumes that range from 50 to 500 µl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., *Proc. Natl. Acad. Sci. U.S.A.* 19, 1614-18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., *Molecular Diversity* 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule that binds to and occupies the active site or a fibronectin domain of the transmembrane serine protease polypeptide, thereby making the active site or fibronectin domain inaccessible to substrate such that normal biological activity is prevented. Examples of such small molecules include, but are not limited to, small peptides or peptide-like molecules. In binding assays, either the test compound or the transmembrane serine protease polypeptide can comprise a detectable label, such as a fluorescent, radioisotopic, chemiluminescent, or enzymatic label, such as horseradish peroxidase, alkaline phosphatase, or luciferase. Detection of a test compound that is bound to the transmembrane serine protease polypeptide can then be accomplished, for example, by direct counting of radioemission, by scintillation counting, or by determining conversion of an appropriate substrate to a detectable product.

Alternatively, binding of a test compound to a transmembrane serine protease polypeptide can be determined without labeling either of the interactants. For example, a microphysiometer can be used to detect binding of a test compound with a target polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a transmembrane serine protease polypeptide. (McConnell et al., *Science* 257, 1906–1912, 1992).

Determining the ability of a test compound to bind to a transmembrane serine protease polypeptide also can be accomplished using a technology such as real-time Bimolecular Interaction Analysis (BIA). Sjolander & Urbaniczky, *Anal. Chem.* 63, 2338–2345, 1991, and Szabo et al., *Curr. Opin. Struct. Biol.* 5, 699–705, 1995. BIA is a technology for studying biospecific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a transmembrane serine protease polypeptide can be used as a "bait protein" in a two-hybrid assay or three-hybrid assay (see, e.g., U.S. Pat. No. 5,283,317; Zervos et al., *Cell* 72, 223–232, 1993; Madura et al., *J. Biol. Chem.* 268, 12046–12054, 1993; Bartel et al., *BioTechniques* 14, 920–924, 1993; Iwabuchi et al., *Oncogene* 8, 1693–1696, 1993; and Brent W094/10300), to identify other proteins which bind to or interact with the transmembrane serine protease polypeptide and modulate its activity.

The two-hybrid system is based on the modular nature of most transcription factors, which consist of separable DNA-binding and activation domains. Briefly, the assay utilizes two different DNA constructs. For example, in one construct a polynucleotide encoding a transmembrane serine protease polypeptide is fused to a polynucleotide encoding the DNA binding domain of a known transcription factor (e.g., GAL-4). In the other construct, a DNA sequence that encodes an unidentified protein ("prey" or "sample") is fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein that interacts with the transmembrane serine protease polypeptide.

It may be desirable to immobilize either the transmembrane serine protease polypeptide (or polynucleotide) or the test compound to facilitate separation of bound from unbound forms of one or both of the interactants, as well as to accommodate automation of the assay. Thus, either the transmembrane serine protease polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the transmembrane serine protease polypeptide (or polynucleotide) or test compound to a solid support, including use of covalent and non-covalent linkages, passive absorption, or pairs of binding moieties attached respectively to the polypeptide or test compound and the solid support. Test compounds are preferably bound to the solid support in an array, so that the location of individual test compounds can be tracked. Binding of a test compound to a transmembrane serine protease polypeptide (or polynucleotide) can be accomplished in any vessel suitable for containing the reactants. Examples of such vessels include microtiter plates, test tubes, and microcentrifuge tubes.

In one embodiment, a transmembrane serine protease polypeptide is a fusion protein comprising a domain that allows the transmembrane serine protease polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed transmembrane serine protease polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing polypeptides or polynucleotides on a solid support also can be used in the screening assays of the invention. For example, either a transmembrane serine protease polypeptide (or polynucleotide) or a test compound can be immobilized utilizing conjugation of biotin and streptavidin. Biotinylated transmembrane serine protease polypeptides or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a transmembrane serine protease polypeptide polynucleotides, or a test compound, but which do not interfere with a desired binding site, such as the active site or a fibronectin domain of the transmembrane serine protease polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the transmembrane serine protease polypeptide (or polynucleotides) or test compound, enzyme-linked assays which rely on detecting a transmembrane serine protease activity of the transmembrane serine protease polypeptide, and SDS gel electrophoresis under non-reducing conditions.

Screening for test compounds which bind to a transmembrane serine protease polypeptide or polynucleotide also can be carried out in an intact cell. Any cell which comprises a transmembrane serine protease polynucleotide or polypeptide can be used in a cell-based assay system. A transmembrane serine protease polynucleotide can be naturally occurring in the cell or can be introduced using techniques such as those described above. Either a primary culture or an established cell line, including neoplastic cell lines such as the colon cancer cell lines HCT116, DLD1, HT29, Caco2, SW837, SW480, and RKO, breast cancer cell lines 21-PT, 21-MT, MDA-468, SK-BR3, and BT-474, the A549 lung cancer cell line, and the H392 glioblastoma cell line, can be used. An intact cell is contacted with a test compound. Binding of the test compound to a transmembrane serine protease polypeptide or polynucleotide is determined as described above, after lysing the cell to release the transmembrane serine protease polypeptide-test compound complex.

Enzyme Assays

Test compounds can be tested for the ability to increase or decrease a transmembrane serine protease activity of a transmembrane serine protease polypeptide. Transmembrane serine protease activity can be measured, for example, using the method described in Example 2. Transmembrane serine protease activity can be measured after contacting either a purified transmembrane serine protease polypeptide, a cell extract, or an intact cell with a test compound. A test compound that decreases transmembrane serine protease activity by at least about 10, preferably about 50, more preferably about 75, 90, or 100% is identified as a potential therapeutic agent for decreasing extracellular matrix degradation. A test compound that increases transmembrane serine protease activity by at least about 10, preferably about 50, more preferably about 75, 90, or 100% is identified as a potential therapeutic agent for increasing extracellular matrix degradation.

Gene Expression

In another embodiment, test compounds that increase or decrease transmembrane serine protease gene expression are identified. A transmembrane serine protease polynucleotide is contacted with a test compound, and the expression of an RNA or polypeptide product of the transmembrane serine protease polynucleotide is determined. The level of expression of transmembrane serine protease mRNA or polypeptide in the presence of the test compound is compared to the level of expression of transmembrane serine protease mRNA or polypeptide in the absence of the test compound. The test compound can then be identified as a modulator of expression based on this comparison. For example, when expression of transmembrane serine protease mRNA or polypeptide is greater in the presence of the test compound than in its absence, the test compound is identified as a stimulator or enhancer of transmembrane serine protease mRNA or polypeptide is less expression. Alternatively, when expression of the mRNA or protein is less in the presence of the test compound than in its absence, the test compound is identified as an inhibitor of transmembrane serine protease mRNA or polypeptide expression.

The level of transmembrane serine protease mRNA or polypeptide expression in the cells can be determined by methods well known in the art for detecting mRNA or protein. Either qualitative or quantitative methods can be used. The presence of polypeptide products of a transmembrane serine protease polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a transmembrane serine protease polypeptide.

Such screening can be carried out either in a cell-free assay system or in an intact cell. Any cell that expresses a transmembrane serine protease polynucleotide can be used in a cell-based assay system. The transmembrane serine protease polynucleotide can be naturally occurring in the cell or can be introduced using techniques such as those described above. Either a primary culture or an established cell line, including neoplastic cell lines such as the colon cancer cell lines HCT116, DLD1, HT29, Caco2, SW837, SW480, and RKO, breast cancer cell lines 21-PT, 21-MT, MDA-468, SK-BR3, and BT-474, the A549 lung cancer cell line, and the H392 glioblastoma cell line, can be used.

Pharmaceutical Compositions

The invention also provides pharmaceutical compositions that can be administered to a patient to achieve a therapeutic effect. Pharmaceutical compositions of the invention can comprise a transmembrane serine protease polypeptide, transmembrane serine protease polynucleotide, antibodies which specifically bind to a transmembrane serine protease polypeptide, or mimetics, agonists, antagonists, or inhibitors of a transmembrane serine protease polypeptide. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents that increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCIENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Therapeutic Indications and Methods

1. Tumor Cell Invasion and Metastasis. Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Agonists and/or antagonists of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

The human transmembrane serine protease gene provides a therapeutic target for decreasing extracellular matrix degradation, in particular for treating or preventing metastatic cancer. For example, blocking a fibronectin domain of human ephrin-like serine protease can suppress or prevent migration or metastasis of tumor cells in response to fibronectin (9, 10). Cancers whose metastasis can be suppressed according to the invention include adenocarcinoma, melanoma, cancers of the adrenal gland, bladder, bone, breast, cervix, gall bladder, liver, lung, ovary, pancreas, prostate, testis, and uterus. Circulating tumor cells arrested in the capillary beds of different organs must invade the endothelial cell lining and degrade its underlying basement membrane (BM) in order to invade into the extravascular tissue(s) where they establish metastasis (1, 2). Metastatic tumor cells often attach at or near the intercellular junctions between adjacent endothelial cells. Such attachment of the metastatic cells is followed by rupture of the junctions, retraction of the endothelial cell borders and migration through the breach in the endothelium toward the exposed underlying BM (1, 11).

Once located between endothelial cells and the BM, the invading cells must degrade the subendothelial glycoproteins and proteoglycans of the BM in order to migrate out of the vascular compartment. Several cellular enzymes (e.g., collagenase IV, plasminogen activator, cathepsin B, elastase) are thought to be involved in degradation of BM (2, 11). Suppression of human transmembrane serine protease activity therefore can be used to suppress tumor cell invasion and metastasis.

2. Tumor Angiogenesis. Basic fibroblast growth factor (bFGF) has been extracted from the subendothelial extracellular matrix produced in vitro (3) and from basement membranes of the cornea (4), suggesting that extracellular matrix may serve as a reservoir for bFGF. Immunohistochemical staining revealed the localization of bFGF in basement membranes of diverse tissues and blood vessels (5). Despite the ubiquitous presence of bFGF in normal tissues, endothelial cell proliferation in these tissues is usually very low, which suggests that bFGF is somehow sequestered from its site of action. It is possible, therefore, that suppression of human transmembrane serine protease activity can suppress release of active bFGF from extracellular matrix and basement membranes. In addition, displacement of bFGF from its storage within basement membranes and extracellular matrix may therefore provide a novel mechanism for induction of neovascularization in normal and pathological situations. Restriction of endothelial cell growth factors in the extracellular matrix may prevent their systemic action on the vascular endothelium, thus maintaining a very low rate of endothelial cells turnover and vessel growth. On the other hand, release of bFGF from storage in the extracellular matrix may elicit localized endothelial cell proliferation and neovascularization in processes such as wound healing, inflammation and tumor development (6, 7).

3. Inflammation and Cellular Immunity. Transmembrane serine protease activity may be involved in the ability of activated cells of the immune system to leave the circulation and elicit both inflammatory and autoimmune responses. Thus, inflammation and cellular immunity may be regulated by regulating activity of transmembrane serine protease.

4. Viral infection. Removal of the cell surface components by transmembrane serine protease may influence the ability of viruses to attach to the cell surface. Regulation of transmembrane serine protease may therefore be used to treat viral infections.

5. Neurodegenerative diseases. It is also possible that transmembrane serine protease activity can be used to degrade, for example, prion protein amyloid plaques of Genstmann-Straussler Syndrome, Creutzfeldt-Jakob disease, and Scrapie.

CNS disorders which may be treated include brain injuries, cerebrovascular diseases and their consequences, Parkinson's disease, corticobasal degeneration, motor neuron disease, dementia, including ALS, multiple sclerosis, traumatic brain injury, stroke, post-stroke, post-traumatic brain injury, and small-vessel cerebrovascular disease. Dementias, such as Alzheimer's disease, vascular dementia, dementia with Lewy bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld-Jakob dementia, HIV dementia, schizophrenia with dementia, and Korsakoff's psychosis also can be treated. Similarly, it may be possible to treat cognitive-related disorders, such as mild cognitive impairment, age-associated memory impairment, age-related cognitive decline, vascular cognitive impairment, attention deficit disorders, attention deficit hyperactivity disorders, and memory disturbances in children with learning disabilities, by regulating the activity of human transmembrane serine protease.

Pain that is associated with CNS disorders also can be treated by regulating the activity of human transmembrane serine protease. Pain which can be treated includes that associated with central nervous system disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neuralgias, and post-herpetic neuralgia. Pain associated with cancer and cancer treatment also can be treated, as can headache pain (for example, migraine with aura, migraine without aura, and other migraine disorders), episodic and chronic tension-type headache, tension-type like headache, cluster headache, and chronic paroxysmal hemicrania.

6. Restenosis and Atherosclerosis. Proliferation of arterial smooth muscle cells (SMCs) in response to endothelial injury and accumulation of cholesterol rich lipoproteins are basic events in the pathogenesis of atherosclerosis and restenosis (8). It is possible that transmembrane serine protease may be involved in the catabolic pathway that may allow substantial cellular and interstitial accumulation of cholesterol rich lipoproteins. The latter pathway is expected to be highly atherogenic by promoting accumulation of apoB and apoE rich lipoproteins (i.e. LDL, VLDL, chylomicrons), independent of feedback inhibition by the cellular sterol content. Altered levels of human transmembrane serine protease activity therefore may inhibit both SMC proliferation and lipid accumulation and thus may halt the progression of restenosis and atherosclerosis.

7. COPD. Chronic obstructive pulmonary (or airways) disease (COPD) is a condition defined physiologically as airflow obstruction that generally results from a mixture of emphysema and peripheral airway obstruction due to chronic bronchitis (Senior & Shapiro, *Pulmonary Diseases and Disorders,* 3d ed., New York, McGraw-Hill, 1998, pp. 659–681, 1998; Barnes, *Chest* 117, 10S–14S, 2000). Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does occur in non-smokers.

Chronic inflammation of the airways is a key pathological feature of COPD (Senior & Shapiro, 1998). The inflammatory cell population comprises increased numbers of macrophages, neutrophils, and CD8+ lymphocytes. Inhaled irritants, such as cigarette smoke, activate macrophages that are resident in the respiratory tract, as well as epithelial cells leading to release of chemokines (e.g., interleukin-8) and other chemotactic factors. These chemotactic factors act to increase the neutrophil/monocyte trafficking from the blood into the lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction, and mucus hypersecretion, all are potential sequelae of this inflammatory response that lead to impaired airflow and gas exchange.

COPD is characterized by damage to the lung extracellular matrix and emphysema can be viewed as the pathologic process that affects the lung parenchyma. This process eventually leads to the destruction of the airway walls resulting in permanent airspace enlargement (Senior and Shapiro, in PULMONARY DISEASES AND DISORDERS, $3^{rd}$ ed., New York, McGraw-Hill, 1998, pp. 659–681, 1998). The observation that inherited deficiency of al-antitrypsin (al-AT), the primary inhibitor of neutrophil elastase, predisposes individuals to early onset emphysema, and that intrapulmonary instillation of elastolytic enzymes in experimental animals causes emphysema, led to the elastase:antielastase hypothesis for the pathogenesis of emphysema (Eriksson, *Acta Med. Scand.* 177(Suppl.), 432, 1965, Gross, *J. Occup. Med.* 6, 481-84, 1964). This in turn led to the concept that destruction of elastin in the lung parenchyma is the basis of the development of emphysema.

A broad range of immune and inflammatory cells including neutrophils, macrophages, T lymphocytes and eosinophils contain proteolytic enzymes that could contribute to the destruction of lung extracellular matrix (Shapiro, 1999). In addition, a number of different classes of proteases have been identified that have the potential to contribute to lung matrix destruction. These include serine proteases, matrix metalloproteinases and cysteine proteases. Of these classes of enzymes, a number can hydrolyze elastin and have been shown to be elevated in COPD patients (neutrophil elastase, MMP-2, 9, 12) (Culpitt et al., *Am. J. Respir. Crit. Care Med.* 160, 1635-39, 1999, Shapiro, *Am. J. Crit. Care Med.* 160 (5), S29–S32, 1999).

It is expected that in the future novel members of the existing classes of proteases and new classes of proteases will be identified that play a significant role in the damage of the extracellular lung matrix including elastin proteolysis. Novel protease targets therefore remain very attractive therapeutic targets.

8. Other therapeutic and diagnostic indications. Anti-human transmembrane serine protease antibodies can be applied for immunodetection and diagnosis of micrometastases, autoimmune lesions, and renal failure in biopsy specimens, plasma samples, and body fluids. Alternatively, if desired a transmembrane serine protease function can be supplied to a cell by introducing a transmembrane serine protease-encoding polynucleotide into the cell.

The invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a polypeptide-binding partner) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects transmembrane serine protease activity can be administered to a human cell, either in vitro or in vivo, to reduce transmembrane serine protease activity. The reagent preferably binds to an expression product of a human transmembrane serine protease gene. If the expression product is a polypeptide, the reagent is preferably an antibody. For treatment of human cells ex vivo, an antibody can be added to a preparation of stem cells that have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung or liver.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about $10^6$ cells, more preferably about 1.0 µg of DNA per 16 nmol of liposome delivered to about $10^6$ cells, and even more preferably about 2.0 µg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a tumor cell, such as a tumor cell ligand exposed on the outer surface of the liposome.

Complexing a liposome with a reagent such as an antisense oligonucleotide or ribozyme can be achieved using methods that are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. *Trends in Biotechnol.* 11, 202-05 (1993); Chiou et al., GENE THERAPEUTICS: METHODS AND APPLICATIONS OF DIRECT GENE TRANSFER (J.A. Wolff, ed.) (1994); Wu & Wu, *J. Biol. Chem.* 263, 621-24 (1988); Wu et al., *J. Biol. Chem.* 269, 542-46 (1994); Zenke et al., *Proc. Natl. Acad. Sci. U.S.A.* 87, 3655-59 (1990); Wu et al., *J. Biol. Chem.* 266, 338-42 (1991).

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE— or calcium phosphate-mediated transfection.

Determination of a Therapeutically Effective Dose

The determination of a therapeutically effective dose is well within the capability of those skilled in the art. A therapeutically effective dose refers to that amount of active ingredient that increases or decreases extracellular matrix degradation relative to that which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides that express antisense oligonucleotides or ribozymes can be introduced into cells by a variety of methods, as described above.

Preferably, a reagent reduces expression of a transmembrane serine protease polynucleotide or activity of a transmembrane serine protease polypeptide by at least about 10, preferably about 50, more preferably about 75, 90, or 100% relative to the absence of the reagent. The effectiveness of the mechanism chosen to decrease the level of expression of a transmembrane serine protease polynucleotide or the activity of a transmembrane serine protease polypeptide can be assessed using methods well known in the art, such as hybridization of nucleotide probes to transmembrane serine protease-specific mRNA, quantitative RT-PCR, immunologic detection of a transmembrane serine protease polypeptide, or measurement of transmembrane serine protease activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

The above disclosure generally describes the present invention, and all patents and patent applications cited in this

EXAMPLE 1
Identification of a Test Compound that Binds to a Transmembrane Serine Protease Polypeptide Purified transmembrane serine protease polypeptides comprising a glutathione-S-transferase protein and absorbed onto glutathione-derivatized wells of 96-well microtiter plates are contacted with test compounds from a small molecule library at pH 7.0 in a physiological buffer solution. Transmembrane serine protease polypeptides comprise an amino acid sequence shown in SEQ ID NO:12 The test compounds comprise a fluorescent tag. The samples are incubated for 5 minutes to one hour. Control samples are incubated in the absence of a test compound.

The buffer solution containing the test compounds is washed from the wells. Binding of a test compound to a transmembrane serine protease polypeptide is detected by fluorescence measurements of the contents of the wells. A test compound that increases the fluorescence in a well by at least 15% relative to fluorescence of a well in which a test compound was not incubated is identified as a compound that binds to a transmembrane serine protease polypeptide.

EXAMPLE 2
Identification of a Test Compound Which Decreases Transmembrane Serine Protease Activity Cellular extracts from the human colon cancer cell line HCT116 are contacted with test compounds from a small molecule library and assayed for transmembrane serine protease activity. Control extracts, in the absence of a test compound, also are assayed. Protease activity can be measured using thiobenzylester substrates, as described in U.S. Pat. No. 5,500,344. For monitoring enzyme activities from granules and column fractions, assays are performed at room temperature using 0.5 mM 5,5'-dithiobis-(2-nitrobenzoic acid) (DTNB) (Sigma) to detect the HSBzl leaving group ($_{410}$=13600M$^{-1}$ cm$^{-1}$).

BLT-esterase activity is estimated using a microtiter assay (Green and Shaw, Anal. Biochem. 93, 223–226, 1979). Briefly, 50 μl of sample is added to 100 μl of 1 mM DTNB, made up in 10 mM HEPES, 1 mM CaCl$_2$, 1 mM MgCl$_2$, pH 7.2. The reaction is initiated by the addition of 50 μl of BLT (Sigma) to give a final concentration of 500 μM. For Metase determinations, 50 μl of dilutions of the sample in 0.1 M HEPES, 0.05 M CaCl$_2$, pH 7.5, are added to 100 μl of 1 mM DTNB, and the reaction is initiated by the addition of 50 μl of Boc-Ala-Ala-Met-S Benzyl (Bzl) to give a final concentration of 150 μM. The duration of the assay depends on color development, the rate of which is measured (O.D.$_{410}$) on a Dynatech MR 5000 microplate reader. Controls of sample and DTNB alone or DTNB and substrate alone are run.

For more sensitive comparisons of enzymatic activities, peptide thiobenzyl ester substrates are used to measure protease activities. The chymase substrate Suc-Phe-Leu-Phe-SBzl is purchased from BACHEM Bioscience Inc., Philadelphia, Pa. Z-Arg-SBzl (the tryptase substrate, Kam et al., J. Biol. Chem. 262, 3444–3451, 1987); Boc-Ala-Ala-AA-SBzl (AA=Asp, Met, Leu, Nle, or Ser), and Suc-Ala-Ala-Met-SBzl (Odake et al, Biochemistry 30, 2217–2227, 1991); Harper et al., Biochemistry 23, 2995–3002, 1984) are synthesized previously. BocAla-Ala-Asp-SBzl is the substrate for Asp-ase and peptide thiobenzyl esters containing Met, Leu or Nle are substrates for Met-ase SP. Assays are performed at room temperature in 0.1 M, HEPES buffer, pH 7.5, containing 0.01 M CaCl$_2$ and 8% Me$_2$O using 0.34 mM 4,4'-dithiodipyridine (Aldrithiol-4, Aldrich Chemical Co., Milwaukee, Wis.) to detect HSBzl leaving group that reacts with 4,4'-dithiodipyridine to release thiopyridone (324= 19800 M$^{-1}$ cm$^{-1}$, Grasetti and Murray, Arch. Biochem. Biophys. 119, 41–49, 1967). The initial rates are measured at 324 nm using a Beckman 35 spectrophotometer when 10–25 μl of an enzyme stock solution is added to a cuvette containing 2.0 ml of buffer, 150 μl of 4,4'-dithiodipyridine, and 25 μl of substrate. The same volume of substrate and 4,4'-dithiodipyridine are added to the reference cell in order to compensate for the background hydrolysis rate of the substrates. Initial rates are measured in duplicate for each substrate concentration and are averaged in each case. Substrate concentrations are 100–133 μM.

A test compound that decreases transmembrane serine protease activity of the extract relative to the control extract by at least 20% is identified as a transmembrane serine protease inhibitor.

EXAMPLE 3
Identification of a Test Compound Which Decreases Transmembrane Serine Protease Gene Expression A test compound is administered to a culture of the breast tumor cell line MDA-468 and incubated at 37° C. for 10 to 45 minutes. A culture of the same type of cells incubated for the same time without the test compound provides a negative control.

RNA is isolated from the two cultures as described in Chirgwin et al., Biochem. 18, 5294-99, 1979). Northern blots are prepared using 20 to 30 μg total RNA and hybridized with a $^{32}$P-labeled transmembrane serine protease-specific probe at 65° C. in Express-hyb (CLONTECH). The probe comprises at least 11 contiguous nucleotides selected from the complement of SEQ ID NO:11. A test compound that decreases the transmembrane serine protease-specific signal relative to the signal obtained in the absence of the test compound is identified as an inhibitor of transmembrane serine protease gene expression.

EXAMPLE 4
Treatment of a Breast Tumor with a Reagent that Specifically Binds to a Transmembrane Serine Protease Gene Product Synthesis of antisense transmembrane serine protease oligonucleotides comprising at least 11 contiguous nucleotides selected from the complement of SEQ ID NO:11 is performed on a Pharmacia Gene Assembler series synthesizer using the phosphoramidite procedure (Uhlmann et al., Chem. Rev. 90, 534-83, 1990). Following assembly and deprotection, oligonucleotides are ethanol-precipitated twice, dried, and suspended in phosphate-buffered saline (PBS) at the desired concentration. Purity of these oligonucleotides is tested by capillary gel electrophoreses and ion exchange HPLC. Endotoxin levels in the oligonucleotide preparation are determined using the Limulus Amebocyte Assay (Bang, Biol. Bull. (Woods Hole, Mass.) 105, 361–362, 1953).

An aqueous composition containing the antisense oligonucleotides at a concentration of 0.1–100 μM is injected directly into a breast tumor with a needle. The needle is placed in the tumors and withdrawn while expressing the aqueous composition within the tumor.

The breast tumor is monitored over a period of days or weeks. Additional injections of the antisense oligonucleotides can be given during that time. Metastasis of the breast tumor is suppressed due to decreased transmembrane serine protease activity of the breast tumor cells.

EXAMPLE 5
Expression of Recombinant Human Transmembrane Serine Protease

The Pichia pastoris expression vector pPICZB (Invitrogen, San Diego, Calif.) is used to produce large quantities of recombinant human transmembrane serine protease polypeptides in yeast. The transmembrane serine protease —encoding DNA sequence is derived from SEQ ID NO:11. Before insertion into vector pPICZB, the DNA sequence is modified by well-known methods in such a way that it contains at its 5'-end an initiation codon and at its 3'-end an enterokinase cleavage site, a His6 reporter tag and a termination codon. Moreover, at both termini recognition sequences for restriction endonucleases are added and after digestion of the multiple cloning site of pPICZ B with the corresponding restriction enzymes the modified DNA sequence is ligated into pPICZ B. This expression vector is designed for inducible expression in *Pichia pastoris*, driven by a yeast promoter. The resulting pPICZ/md-His6 vector is used to transform the yeast.

The yeast is cultivated under usual conditions in 5 liter shake flasks and the recombinantly produced protein isolated from the culture by affinity chromatography (Ni-NTA-Resin) in the presence of 8 M urea. The bound polypeptide is eluted with buffer, pH 3.5, and neutralized. Separation of the polypeptide from the His6 reporter tag is accomplished by site-specific proteolysis using enterokinase (Invitrogen, San Diego, Calif.) according to manufacturer's instructions. Purified human transmembrane serine protease polypeptide is obtained.

EXAMPLE 6
Proliferation Inhibition Assay: Antisense Oligonucleotides Suppress the Growth of Cancer Cell Lines The cell line used for testing is the human colon cancer cell line HCT116. Cells are cultured in RPMI-1640 with 10–15% fetal calf serum at a concentration of 10,000 cells per milliliter in a volume of 0.5 ml and kept at 37° C. in a 95% air/5%$CO_2$ atmosphere.

Phosphorothioate oligoribonucleotides are synthesized on an Applied Biosystems Model 380B DNA synthesizer using phosphoroamidite chemistry. A sequence of 24 bases complementary to the nucleotides at position 1 to 24 of SEQ ID NO:11 is used as the test oligonucleotide. As a control, another (random) sequence is used: 5'-TCA ACT GAC TAG ATG TAC ATG GAC-3' (SEQ ID NO:36). Following assembly and deprotection, oligonucleotides are ethanol-precipitated twice, dried, and suspended in phosphate buffered saline at the desired concentration. Purity of the oligonucleotides is tested by capillary gel electrophoresis and ion exchange HPLC. The purified oligonucleotides are added to the culture medium at a concentration of 10 $\mu$M once per day for seven days.

The addition of the test oligonucleotide for seven days results in significantly reduced expression of human transmembrane serine protease as determined by Western blotting. This effect is not observed with the control oligonucleotide. After 3 to 7 days, the number of cells in the cultures is counted using an automatic cell counter. The number of cells in cultures treated with the test oligonucleotide (expressed as 100%) is compared with the number of cells in cultures treated with the control oligonucleotide. The number of cells in cultures treated with the test oligonucleotide is not more than 30% of control, indicating that the inhibition of human transmembrane serine protease has an anti-proliferative effect on cancer cells.

EXAMPLE 7
In Vivo Testing of Compounds/Target Validation

1. Acute Mechanistic Assays 1.1. Reduction in Mitogenic Plasma Hormone Levels

This non-tumor assay measures the ability of a compound to reduce either the endogenous level of a circulating hormone or the level of hormone produced in response to a biologic stimulus. Rodents are administered test compound (p.o., i.p., i.v., i.m., or s.c.). At a predetermined time after administration of test compound, blood plasma is collected. Plasma is assayed for levels of the hormone of interest. If the normal circulating levels of the hormone are too low and/or variable to provide consistent results, the level of the hormone may be elevated by a pretreatment with a biologic stimulus (i.e., LHRH may be injected i.m. into mice at a dosage of 30 ng/mouse to induce a burst of testosterone synthesis). The timing of plasma collection would be adjusted to coincide with the peak of the induced hormone response. Compound effects are compared to a vehicle-treated control group. An F-test is preformed to determine if the variance is equal or unequal followed by a Student's t-test. Significance is p value$\leq$0.05 compared to the vehicle control group.

1.2. Hollow Fiber Mechanism of Action Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol, these may include assays for gene expression (bDNA, PCR, or Taqman), or a specific biochemical activity (i.e., cAMP levels. Results are analyzed by Student's t-test or Rank Sum test after the variance between groups is compared by an F-test, with significance at p$\leq$0.05 as compared to the vehicle control group.

2. Subacute Functional In Vivo Assays 2.1. Reduction in Mass of Hormone Dependent Tissues This is another non-tumor assay that measures the ability of a compound to reduce the mass of a hormone dependent tissue (i.e., seminal vesicles in males and uteri in females). Rodents are administered test compound (p.o., i.p., i.v., i.m., or s.c.) according to a predetermined schedule and for a predetermined duration (i.e., 1 week). At termination of the study, animals are weighed, the target organ is excised, any fluid is expressed, and the weight of the organ is recorded. Blood plasma may also be collected. Plasma may be assayed for levels of a hormone of interest or for levels of test agent. Organ weights may be directly compared or they may be normalized for the body weight of the animal. Compound effects are compared to a vehicle-treated control group. An F-test is preformed to determine if the variance is equal or unequal followed by a Student's t-test. Significance is p value$\leq$0.05 compared to the vehicle control group.

2.2. Hollow Fiber Proliferation Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol. Cell proliferation is determined by measuring a marker of cell number (i.e., MTT or LDH). The cell number and change in cell number from the starting inoculum are analyzed by Student's t-test or Rank Sum test after the variance between groups is compared by an F-test, with significance at p$\leq$0.05 as compared to the vehicle control group.

2.3. Anti-Angiogenesis Models 2.3.1. Corneal Angiogenesis

Hydron pellets with or without growth factors or cells are implanted into a micropocket surgically created in the rodent cornea. Compound administration may be systemic or local (compound mixed with growth factors in the hydron pellet). Corneas are harvested at 7 days post implantation immediately following intracardiac infusion of colloidal carbon and are fixed in 10% formalin. Readout is qualitative scoring and/or image analysis. Qualitative scores are compared by Rank Sum test. Image analysis data is evaluated by measuring the area of neovascularization (in pixels) and group averages are compared by Student's t-test (2 tail). Significance is $p \leq 0.05$ as compared to the growth factor or cells only group.

2.3.2. Matrigel Angiogenesis

Matrigel, containing cells or growth factors, is injected subcutaneously. Compounds are administered p.o., i.p., i.v., i.m., or s.c. Matrigel plugs are harvested at predetermined time point(s) and prepared for readout. Readout is an ELISA-based assay for hemoglobin concentration and/or histological examination (i.e. vessel count, special staining for endothelial surface markers: CD31, factor-8). Readouts are analyzed by Student's t-test, after the variance between groups is compared by an F-test, with significance determined at $p \leq 0.05$ as compared to the vehicle control group.

3. Primary Antitumor Efficacy
3.1. Early Therapy Models
3.1.1. Subcutaneous Tumor Tumor cells or fragments are implanted subcutaneously on Day 0. Vehicle and/or compounds are administered p.o., i.p., i.v., i.m., or s.c. according to a predetermined schedule starting at a time, usually on Day 1, prior to the ability to measure the tumor burden. Body weights and tumor measurements are recorded 2–3 times weekly. Mean net body and tumor weights are calculated for each data collection day. Anti-tumor efficacy may be initially determined by comparing the size of treated (T) and control (C) tumors on a given day by a Student's t-test, after the variance between groups is compared by an F-test, with significance determined at $p \leq 0.05$. The experiment may also be continued past the end of dosing in which case tumor measurements would continue to be recorded to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is $p \leq 0.05$.

3.1.2. Intraperitoneal/Intracranial Tumor Models

Tumor cells are injected intraperitoneally or intracranially on Day 0. Compounds are administered p.o., i.p., i.v., i.m., or s.c. according to a predetermined schedule starting on Day 1. Observations of morbidity and/or mortality are recorded twice daily. Body weights are measured and recorded twice weekly. Morbidity/mortality data is expressed in terms of the median time of survival and the number of long-term survivors is indicated separately. Survival times are used to generate Kaplan-Meier curves. Significance is $p \leq 0.05$ by a log-rank test compared to the control group in the experiment.

3.2. Established Disease Model

Tumor cells or fragments are implanted subcutaneously and grown to the desired size for treatment to begin. Once at the predetermined size range, mice are randomized into treatment groups. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group. Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group.

3.3. Orthotopic Disease Models
3.3.1. Mammary Fat Pad Assay

Tumor cells or fragments, of mammary adenocarcinoma origin, are implanted directly into a surgically exposed and reflected mammary fat pad in rodents. The fat pad is placed back in its original position and the surgical site is closed. Hormones may also be administered to the rodents to support the growth of the tumors. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group.

Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group. In addition, this model provides an opportunity to increase the rate of spontaneous metastasis of this type of tumor. Metastasis can be assessed at termination of the study by counting the number of visible foci per target organ, or measuring the target organ weight. The means of these endpoints are compared by Student's t-test after conducting an F-test, with significance determined at $p \leq 0.05$ compared to the control group in the experiment.

3.3.2. Intraprostatic Assay

Tumor cells or fragments, of prostatic adenocarcinoma origin, are implanted directly into a surgically exposed dorsal lobe of the prostate in rodents. The prostate is externalized through an abdominal incision so that the tumor can be implanted specifically in the dorsal lobe while verifying that the implant does not enter the seminal vesicles. The successfully inoculated prostate is replaced in the abdomen and the incisions throught e abdomen and skin are closed. Hormones may also be administered to the rodents to support the growth of the tumors. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the lungs), or measuring the target organ weight (i.e., the regional lymph nodes). The means of these endpoints are compared by Student's t-test after conducting an F-test, with significance determined at $p \leq 0.05$ compared to the control group in the experiment.

3.3.3. Intrabronchial Assay

Tumor cells of pulmonary origin may be implanted intrabronchially by making an incision through the skin and exposing the trachea. The trachea is pierced with the beveled end of a 25 gauge needle and the tumor cells are inoculated into the main bronchus using a flat-ended 27 gauge needle with a 90° bend. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the contralateral lung), or measuring the target organ weight. The means of these endpoints are compared by Student's t-test after conducting an F-test, with significance determined at $p \leq 0.05$ compared to the control group in the experiment.

3.3.4. Intracecal Assay

Tumor cells of gastrointestinal origin may be implanted intracecally by making an abdominal incision through the skin and externalizing the intestine. Tumor cells are inoculated into the cecal wall without penetrating the lumen of the intestine using a 27 or 30 gauge needle. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the liver), or measuring the target organ weight. The means of these endpoints are compared by Student's t-test after conducting an F-test, with significance determined at $p \leq 0.05$ compared to the control group in the experiment.

4. Secondary (Metastatic) Antitumor Efficacy

4.1. Spontaneous Metastasis

Tumor cells are inoculated s.c. and the tumors allowed to grow to a predetermined range for spontaneous metastasis studies to the lung or liver. These primary tumors are then excised. Compounds are administered p.o., i.p., i.v., i.m., or s.c. according to a predetermined schedule which may include the period leading up to the excision of the primary tumor to evaluate therapies directed at inhibiting the early stages of tumor metastasis. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance determined at $p \leq 0.05$ compared to the control group in the experiment for both of these endpoints.

4.2. Forced Metastasis

Tumor cells are injected into the tail vein, portal vein, or the left ventricle of the heart in experimental (forced) lung, liver, and bone metastasis studies, respectively. Compounds are administered p.o., i.p., i.v., i.m., or s.c. according to a predetermined schedule. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance at $p \leq 0.05$ compared to the vehicle control group in the experiment for both endpoints.

EXAMPLE 8

In Vivo Testing of Compounds/Target Validation

1. Pain:

Acute Pain

Acute pain is measured on a hot plate mainly in rats. Two variants of hot plate testing are used: In the classical variant animals are put on a hot surface (52 to 56 C) and the latency time is measured until the animals show nocifensive behavior, such as stepping or foot licking. The other variant is an increasing temperature hot plate where the experimental animals are put on a surface of neutral temperature. Subsequently this surface is slowly but constantly heated until the animals begin to lick a hind paw. The temperature which is reached when hind paw licking begins is a measure for pain threshold.

Compounds are tested against a vehicle treated control group. Substance application is performed at different time points via different application routes (i.v., i.p., p.o., i.t., i.c.v., s.c., intradermal, transdermal) prior to pain testing.

Persistent Pain

Persistent pain is measured with the formalin or capsaicin test, mainly in rats. A solution of 1 to 5% formalin or 10 to 100 µg capsaicin is injected into one hind paw of the experimental animal. After formalin or capsaicin application the animals show of nocifensive reactions like flinching, licking and biting of the affected paw. The number of nocifensive reactions within a time frame of up to 90 minutes is a measure for intensity of pain.

Compounds are tested against a vehicle treated control group. Substance application is performed at different time points via different application routes (i.v., i.p., p.o., i.t., i.c.v., s.c., intradermal, transdermal) prior to formalin or capsaicin administration.

Neuropathic Pain

Neuropathic pain is induced by different variants of unilateral sciatic nerve injury mainly in rats. The operation is performed under anesthesia. The first variant of sciatic nerve injury is produced by placing loosely constrictive ligatures around the common sciatic nerve. The second variant is the tight ligation of about the half of the diameter of the common sciatic nerve. In the next variant, a group of models is used in which tight ligations or transections are made of either the L5 and L6 spinal nerves, or the L % spinal nerve only. The fourth variant involves an axotomy of two of the three terminal branches of the sciatic nerve (tibial and common peroneal nerves) leaving the remaining sural nerve intact whereas the last variant comprises the axotomy of only the tibial branch leaving the sural and common nerves uninjured. Control animals are treated with a sham operation.

Postoperatively, the nerve injured animals develop a chronic mechanical allodynia, cold allodynioa, as well as a thermal hyperalgesia. Mechanical allodynia is measured by means of a pressure transducer (electronic von Frey Anesthesiometer, IITC Inc.-Life Science Instruments, Woodland Hills, SA, USA; Electronic von Frey System, Somedic Sales AB, Hörby, Sweden). Thermal hyperalgesia is measured by means of a radiant heat source (Plantar Test, Ugo Basile, Comerio, Italy), or by means of a cold plate of 5 to 10 C where the nocifensive reactions of the affected hind paw are counted as a measure of pain intensity. A further test for cold induced pain is the counting of nocifensive reactions, or duration of nocifensive responses after plantar administration of acetone to the affected hind limb. Chronic pain in general is assessed by registering the circadanian rhytms in activity (Suio and Arndt, Universität zu Köln, Cologne, Germany), and by scoring differences in gait (foot print patterns; FOOTPRINTS program, Klapdor et al., 1997. A low cost method to analyse footprint patterns. J. Neurosci. Methods 75, 49–54).

Compounds are tested against sham operated and vehicle treated control groups. Substance application is performed at different time points via different application routes (i.v., i.p., p.o., i.t., i.c.v., s.c., intradermal, transdermal) prior to pain testing.

Inflammatory Pain

Inflammatory pain is induced mainly in rats by injection of 0.75 mg carrageenan or complete Freund's adjuvant into one hind paw. The animals develop an edema with mechanical allodynia as well as thermal hyperalgesia. Mechanical allodynia is measured by means of a pressure transducer (electronic von Frey Anesthesiometer, IITC Inc.-Life Science Instruments, Woodland Hills, SA, USA). Thermal hyperalgesia is measured by means of a radiant heat source (Plantar Test, Ugo Basile, Comerio, Italy, Paw thermal stimulator, G. Ozaki, University of California, USA). For edema measurement two methods are being used. In the first method, the animals are sacrificed and the affected hindpaws sectioned and weighed. The second method comprises differences in paw volume by measuring water displacement in a plethysmometer (Ugo Basile, Comerio, Italy).

Compounds are tested against uninflamed as well as vehicle treated control groups. Substance application is performed at different time points via different application routes (i.v., i.p., p.o., i.t., i.c.v., s.c., intradermal, transdermal) prior to pain testing.

Diabetic Neuropathic Pain

Rats treated with a single intraperitoneal injection of 50 to 80 mg/kg streptozotocin develop a profound hyperglycemia and mechanical allodynia within 1 to 3 weeks. Mechanical allodynia is measured by means of a pressure transducer (electronic von Frey Anesthesiometer, IITC Inc.-Life Science Instruments, Woodland Hills, SA, USA).

Compounds are tested against diabetic and non-diabetic vehicle treated control groups. Substance application is performed at different time points via different application routes (i.v., i.p., p.o., i.t., i.c.v., s.c., intradermal, transdermal) prior to pain testing.

2. Parkinson's Disease

6-Hydroxydopamine (6-OH-DA) Lesion

Degeneration of the dopaminergic nigrostriatal and striatopallidal pathways is the central pathological event in Parkinson's disease. This disorder has been mimicked experimentally in rats using single/sequential unilateral stereotaxic injections of 6-OH-DA into the medium forebrain bundle (MFB).

Male Wistar rats (Harlan Winkelmann, Germany), weighing 200±250 g at the beginning of the experiment, are used. The rats are maintained in a temperature- and humidity-controlled environment under a 12 h light/dark cycle with free access to food and water when not in experimental sessions. The following in vivo protocols are approved by the governmental authorities. All efforts are made to minimize animal suffering, to reduce the number of animals used, and to utilize alternatives to in vivo techniques.

Animals are administered pargyline on the day of surgery (Sigma, St. Louis, MO., USA; 50 mg/kg i.p.) in order to inhibit metabolism of 6-OHDA by monoamine oxidase and desmethylimipramine HCl (Sigma; 25 mg/kg i.p.) in order to prevent uptake of 6-OHDA by noradrenergic terminals. Thirty minutes later the rats are anesthetized with sodium pentobarbital (50 mg/kg) and placed in a stereotaxic frame. In order to lesion the DA nigrostriatal pathway 4 $\mu$l of 0.01% ascorbic acid-saline containing 8 $\mu$g of 6-OHDA HBr (Sigma) are injected into the left medial fore-brain bundle at a rate of 1 $\mu$l/min (2.4 mm anterior, 1.49 mm lateral, −2.7 mm ventral to Bregma and the skull surface). The needle is left in place an additional 5 min to allow diffusion to occur.

Stepping Test

Forelimb akinesia is assessed three weeks following lesion placement using a modified stepping test protocol. In brief, the animals are held by the experimenter with one hand fixing the hindlimbs and slightly raising the hind part above the surface. One paw is touching the table, and is then moved slowly sideways (5 s for 1 m), first in the forehand and then in the backhand direction. The number of adjusting steps is counted for both paws in the backhand and forehand direction of movement. The sequence of testing is right paw forehand and backhand adjusting stepping, followed by left paw forehand and backhand directions. The test is repeated three times on three consecutive days, after an initial training period of three days prior to the first testing. Forehand adjusted stepping reveals no consistent differences between lesioned and healthy control animals. Analysis is therefore restricted to backhand adjusted stepping.

Balance Test

Balance adjustments following postural challenge are also measured during the stepping test sessions. The rats are held in the same position as described in the stepping test and, instead of being moved sideways, tilted by the experimenter towards the side of the paw touching the table. This maneuver results in loss of balance and the ability of the rats to regain balance by forelimb movements is scored on a scale ranging from 0 to 3. Score 0 is given for a normal forelimb placement. When the forelimb movement is delayed but recovery of postural balance detected, score 1 is given. Score 2 represents a clear, yet insufficient, forelimb reaction, as evidenced by muscle contraction, but lack of success in recovering balance, and score 3 is given for no reaction of movement. The test is repeated three times a day on each side for three consecutive days after an initial training period of three days prior to the first testing.

Staircase Test (Paw Reaching)

A modified version of the staircase test is used for evaluation of paw reaching behavior three weeks following primary and secondary lesion placement. Plexiglass test boxes with a central platform and a removable staircase on each side are used. The apparatus is designed such that only the paw on the same side at each staircase can be used, thus providing a measure of independent forelimb use. For each test the animals are left in the test boxes for 15 min. The double staircase is filled with 7×3 chow pellets (Precision food pellets, formula: P, purified rodent diet, size 45 mg; Sandown Scientific) on each side. After each test the number of pellets eaten (successfully retrieved pellets) and the number of pellets taken (touched but dropped) for each paw and the success rate (pellets eaten/pellets taken) are counted separately. After three days of food deprivation (12 g per animal per day) the animals are tested for 11 days. Full analysis is conducted only for the last five days.

MPTP Treatment

The neurotoxin 1-methyl-4-phenyl-1,2,3,6-tetrahydropyridine (MPTP) causes degeneration of mesencephalic dopaminergic (DAergic) neurons in rodents, non-human primates, and humans and, in so doing, reproduces many of the symptoms of Parkinson's disease. MPTP leads to a marked decrease in the levels of dopamine and its metabolites, and in the number of dopaminergic terminals in the striatum as well as severe loss of the tyrosine hydroxylase (TH)-immunoreactive cell bodies in the substantia nigra, pars compacta.

In order to obtain severe and long-lasting lesions, and to reduce mortality, animals receive single injections of MPTP, and are then tested for severity of lesion 7–10 days later. Successive MPTP injections are administered on days 1, 2 and 3. Animals receive application of 4 mg/kg MPTP hydrochloride (Sigma) in saline once daily. All injections are intraperitoneal (i.p.) and the MPTP stock solution is frozen between injections. Animals are decapitated on day 11.

Immunohistology

At the completion of behavioral experiments, all animals are anaesthetized with 3 ml thiopental (1 g/40 ml i.p., Tyrol Pharma). The mice are perfused transcardially with 0.01 M PBS (pH 7.4) for 2 min, followed by 4% paraformaldehyde (Merck) in PBS for 15 min. The brains are removed and placed in 4% paraformaldehyde for 24 h at 4° C. For dehydration they are then transferred to a 20% sucrose (Merck) solution in 0.1 M PBS at 4° C. until they sink. The brains are frozen in methylbutan at −20° C. for 2 min and stored at −70° C. Using a sledge microtome (mod. 3800-Frigocut, Leica), 25 $\mu$m sections are taken from the genu of the corpus callosum (AP 1.7 mm) to the hippocampus (AP 21.8 mm) and from AP 24.16 to AP 26.72. Forty-six sections are cut and stored in assorters in 0.25 M Tris buffer (pH 7.4) for immunohistochemistry.

A series of sections is processed for free-floating tyrosine hydroxylase (TH) immunohistochemistry. Following three rinses in 0.1 M PBS, endogenous peroxidase activity is quenched for 10 min in 0.3% $H_2O_2$±PBS. After rinsing in PBS, sections are preincubated in 10% normal bovine serum (Sigma) for 5 min as blocking agent and transferred to either primary anti-rat TH rabbit antiserum (dilution 1:2000).

Following overnight incubation at room temperature, sections for TH immunoreactivity are rinsed in PBS (2×10 min) and incubated in biotinylated anti-rabbit immunoglobulin G raised in goat (dilution 1:200) (Vector) for 90 min, rinsed repeatedly and transferred to Vectastain ABC (Vector) solution for 1 h. 3, 3'-Diaminobenzidine tetrahydrochloride (DAB; Sigma) in 0.1 M PBS, supplemented with 0.005% $H_2O_2$, serves as chromogen in the subsequent visualization reaction. Sections are mounted on to gelatin-coated slides, left to dry overnight, counter-stained with hematoxylin dehydrated in ascending alcohol concentrations and cleared in butylacetate. Coverslips are mounted on entellan.

Rotarod Test

We use a modification of the procedure described by Rozas and Labandeira-Garcia (1997), with a CR-1 Rotamex system (Columbus Instruments, Columbus, Ohio.) comprising an IBM-compatible personal computer, a CIO-24 data acquisition card, a control unit, and a four-lane rotarod unit. The rotarod unit consists of a rotating spindle (diameter 7.3 cm) and individual compartments for each mouse. The system software allows preprogramming of session protocols with varying rotational speeds (0–80 rpm). Infrared beams are used to detect when a mouse has fallen onto the base grid beneath the rotarod. The system logs the fall as the end of the experiment for that mouse, and the total time on the rotarod, as well as the time of the fall and all the set-up parameters, are recorded. The system also allows a weak current to be passed through the base grid, to aid training.

3. Dementia

The Object Recognition Task

The object recognition task has been designed to assess the effects of experimental manipulations on the cognitive performance of rodents. A rat is placed in an open field, in which two identical objects are present. The rats inspects both objects during the first trial of the object recognition task. In a second trial, after a retention interval of for example 24 hours, one of the two objects used int the first trial, the 'familiar' object, and a novel object are placed in the open field. The inspection time at each of the objects is registered. The basic measures in the OR task is the time spent by a rat exploring the two object the second trial. Good retention is reflected by higher exploritation times towards the novel than the 'familiar' object.

Administration of the putative cognition enhancer prior to the first trial predominantly allows assessment of the effects on acquisition, and eventually on consolidation processes. Administration of the testing compound after the first trial allows to assess the effects on consolidation processes, whereas administration before the second trial allows to measure effects on retrieval processes.

The Passive Avoidance Task

The passive avoidance task assesses memory performance in rats and mice. The inhibitory avoidance apparatus consists of a two-compartment box with a light compartment and a dark compartment. The two compartments are separated by a guillotine door that can be operated by the experimenter. A threshold of 2 cm separates the two compartments when the guillotine door is raised. When the door is open, the illumination in the dark compartment is about 2 lux. The light intensity is about 500 lux at the center of the floor of the light compartment.

Two habituation sessions, one shock session, and a retention session are given, separated by inter-session intervals of 24 hours. In the habituation sessions and the retention session the rat is allowed to explore the apparatus for 300 sec. The rat is placed in the light compartment, facing the wall opposite to the guillotine door. After an accommodation period of 15 sec. the guillotine door is opened so that all parts of the apparatus can be visited freely. Rats normally avoid brighly lit areas and will enter the dark compartment within a few seconds.

In the shock session the guillotine door between the compartments is lowered as soon as the rat has entered the dark compartment with its four paws, and a scrambled 1 mA footshock is administered for 2 sec. The rat is removed from the apparatus and put back into its home cage. The procedure during the retention session is identical to that of the habituation sessions.

The step-through latency, that is the first latency of entering the dark compartment (in sec.) during the retention session is an index of the memory performance of the animal; the longer the latency to enter the dark compartment, the better the retention is. A testing compound in given half an hour before the shock session, together with 1 mg*kg$^{-1}$ scopolamine. Scopolamine impairs the memory performance during the retention session 24 hours later. If the test compound increases the enter latency compared with the scopolamine-treated controls, is is likely to possess cognition enhancing potential.

The Morris Water Escape Task

The Morris water escape task measures spatial orientation learning in rodents. It is a test system that has extensively been used to investigate the effects of putative therapeutic on the cognitive functions of rats and mice. The performance of an animal is assessed in a circular water tank with an escape platform that is submerged about 1 cm below the surface of the water. The escape platform is not visible for an animal swimming in the water tank. Abundant extra-maze cues are provided by the furniture in the room, including desks, computer equipment, a second water tank, the presence of the experimenter, and by a radio on a shelf that is playing softly.

The animals receive four trials during five daily acquisition sessions. A trial is started by placing an animal into the pool, facing the wall of the tank. Each of four starting positions in the quadrants north, east, south, and west is used once in a series of four trials; their order is randomized. The escape platform is always in the same position. A trial is terminated as soon as the animal had climbs onto the escape platform or when 90 seconds have elapsed, whichever event occurs first. The animal is allowed to stay on the platform for 30 seconds. Then it is taken from the platform and the next trial is started. If an animal did not find the platform within 90 seconds it is put on the platform by the experimenter and is allowed to stay there for 30 seconds. After the fourth trial of the fifth daily session, an additional trial is given as a probe trial: the platform is removed, and the time the animal spends in the four quadrants is measured for 30 or 60 seconds. In the probe trial, all animals start from the same start position, opposite to the quadrant where the escape platform had been positioned during acquisition.

Four different measures are taken to evaluate the performance of an animal during acquisition training: escape latency, traveled distance, distance to platform, and swimming speed. The following measures are evaluated for the probe trial: time (s) in quadrants and traveled distance (cm) in the four quadrants. The probe trial provides additional information about how well an animal learned the position of the escape platform. If an animal spends more time and swims a longer distance in the quadrant where the platform had been positioned during the acquisition sessions than in any other quadrant, one concludes that the platform position has been learned well.

In order to assess the effects of putative cognition enhancing compounds, rats or mice with specific brain lesions that impair cognitive functions, or animals treated with compounds such as scopolamine or MK-801, which interfere with normal learning, or aged animals which suffer from cognitive deficits, are used.

The T-Maze Spontaneous Alternation Task

The T-maze spontaneous alternation task (TeMCAT) assesses the spatial memory performance in mice. The start arm and the two goal arms of the T-maze are provided with guillotine doors which can be operated manually by the experimenter. A mouse is put into the start arm at the beginning of training. The guillotine door is closed. In the first trial, the 'forced trial', either the left or right goal arm is blocked by lowering the guillotine door. After the mouse has been released from the start arm, it will negotiate the maze, eventually enter the open goal arm, and return to the start position, where it will be confined for 5 seconds, by lowering the guillotine door. Then, the animal can choose freely between the left and right goal arm (all guillotine-doors opened) diring 14 'free choice' trials. As soon a the mouse has entered one goal arm, the other one is closed. The mouse eventually returns to the start arm and is free to visit whichever goalarm it wants after having been confined to the start arm for 5 seconds. After completion of 14 free choice trials in one session, the animal is removed from the maze. During training, the animal is never handeled.

The per-cent alternations out of 14 trials is calculated. This percentage and the total time needed to complete the first forced trial and the subsequent 14 free choice trials (in s) is analyzed. Cognitive deficits are usually induced by an injection of scopolamine, 30 min before the start of the training session. Scopolamine reduced the per-cent alternations to chance level, or below. A cognition enhancer, which is always administered before the training session, will at least partially, antagonize the scopolamine-induced reduction in the spontaneous alternation rate.

EXAMPLE 9

Tissue-Specific Expression of Transmembrane Serine Protease

As a first step to establishing a role for transmembrane serine protease in the pathogenesis of COPD, expression profiling of the gene was done using real-time quantitative PCR with RNA samples from human respiratory tissues and inflammatory cells relevant to COPD. The panel consisted of total RNA samples lung (adult and fetal), trachea, freshly isolated alveolar type II cells, cultured human bronchial epithelial cells, cultured small airway epithelial cells, cultured bronchial sooth muscle cells, cultured H441 cells (Clara-like), freshly isolated neutrophils and monocytes, and cultured monocytes (macrophage-like). Expression of transmembrane serine protease also was evaluated in a range of human tissues using total RNA panels obtained from Clontech Laboratories, UK, Ltd. The tissues were adrenal gland, bone marrow, brain, colon, heart, kidney, liver, lung, mammary gland, pancreas, prostate, salivary gland, skeletal muscle, small intestine, spleen, stomach, testis, thymus, trachea, thyroid, and uterus.

Real-time quantitative PCR. Expression profiling of the target gene was performed using real-time quantitative PCR, a development of the kinetic analysis of PCR first described in Higuchi et al., *BioTechnology* 10, 413-17, 1992, and Higuchi et al., *BioTechnology* 11, 1026-30, 1993. The principle is that at any given cycle within the exponential phase of PCR, the amount of product is proportional to the initial number of template copies.

PCR amplification is performed in the presence of an oligonucleotide probe (TaqMan probe) that is complementary to the target sequence and labeled with a fluorescent reporter dye and a quencher dye. During the extension phase of PCR, the probe is cleaved by the 5'-3' endonuclease activity of Taq DNA polymerase, releasing the fluorophore from the effect of the quenching dye (Holland et al., *Proc. Natl. Acad. Sci. U.S.A.* 88, 7276-80, 1991). Because the fluorescence emission increases in direct proportion to the amount of the specific amplified product, the exponential growth phase of PCR product can be detected and used to determine the initial template concentration (Heid et al., *Genome Res.* 6, 986-94, 1996, and Gibson et al., *Genome Res.* 6, 995–1001, 1996).

Real-time quantitative PCR was done using an ABI Prism 7700 Sequence Detector. The $C_T$ value generated for each reaction was used to determine the initial template concentration (copy number) by interpolation from a universal standard curve. The level of expression of the target gene in each sample was calculated relative to the sample with the lowest expression of the gene.

RNA extraction and cDNA preparation. Total RNA from each of the respiratory tissues and inflammatory cell types listed above were isolated using Qiagen's RNeasy system according to the manufacturer's protocol (Crawley, West Sussex, UK). The concentration of purified RNA was determined using a RiboGreen RNA quantitation kit (Molecular Probes Europe, The Netherlands). For the preparation of cDNA, 1 µg of total RNA was reverse transcribed in a final volume of 20 µl, using 200 U of SUPERSCRIPT™ RNase H Reverse Transcriptase (Life Technologies, Paisley, UK), 10 mM dithiothreitol, 0.5 mM of each dNTP and 5 µM random hexamers (Applied Biosystems, Warrington, Cheshire, UK) according to the manufacturer's protocol.

TaqMan quantitative analysis. Specific primers and probe were designed according to the recommendations of PE Applied Biosystems. The probe was labeled at the 5' end with FAM (6-carboxyfluorescein). Quantification PCR was performed with 5 ng of reverse transcribed RNA from each sample. Each determination is done in duplicate.

The assay reaction mix was as follows: 1X final TaqMan Universal PCR Master Mix (from 2X stock) (PE Applied Biosystems, Calif.); 900 nM forward primer; 900 nM reverse primer; 200 nM probe; 5 ng cDNA; and water to 25 µl.

Each of the following steps were carried out once: pre PCR, 2 minutes at 50° C., and 10 minutes at 95° C. The following steps are carried out 40 times: denaturation, 15 seconds at 95° C., annealing/extension, 1 minute at 60° C.

All experiments were performed using an ABI Prism 7700 Sequence Detector (PE Applied Biosystems, Calif.). At the end of the run, fluorescence data acquired during PCR were processed as described in the ABI Prism 7700 user's manual to achieve better background subtraction as well as signal linearity with the starting target quantity.

Tables 1 and 2 show the results of expression profiling for transmembrane serine protease using the indicated cell and tissue samples. For Table 1, the cells are defined as follows: HBEC, cultured human bronchial epithelial cells; H441, a Clara-like cell line; SAE, cultured small airway epithelial cells; SMC, cultured airway smooth muscle cells; AII, freshly isolated human alveolar type II cells; Neut, freshly isolated circulating neutrophils; Mono, freshly isolated monocytes; and CM, cultured monocytes. Other letters identify the donor. The results are shown graphically in FIGS. 2 and 3.

TABLE 1

| Tissue | Relative expression |
| --- | --- |
| Lung | 2200.562359 |
| Trachea | 258.4435393 |
| HBEC 1 | 513.406875 |
| HBEC 2 | 780.9633981 |
| H441 | 5636.839641 |
| SMC | 0 |
| SAE | 4154.786196 |
| AII | 1428.383024 |
| Fetal lung | 59.1577544 |
| COPD Neut 1 | 2.529186063 |
| COPD Neut 2 | 1 |
| COPD Neut 4 | 8.733909349 |
| GAP Neut | 5.889527853 |
| AEM Neut | 0 |
| AT Neut | 2.529186063 |
| KN Neut | 0 |
| SM Mono | 31.93586472 |
| DLF Mono | 26.90014866 |
| DS Mono | 110.9856117 |
| RLH CM | 59.91460217 |
| CTP CM | 158.4289996 |

TABLE 2

| Tissue | Relative expression |
| --- | --- |
| Adrenal gland | 13.45548325 |
| Bone Marrow | 18.60661194 |
| Brain | 5.186534845 |
| Colon | 43.05318645 |
| Heart | 6.118448375 |
| HL60 | 1 |
| Kidney | 23.68930394 |
| Liver | 1.705502263 |
| Lung | 144.941683 |
| Mammary gland | 128.454789 |
| Pancreas | 27.59276994 |
| Prostate | 32.75814493 |
| Salivary gland | 129.273736 |
| Skeletal Muscle | 35.57961956 |
| Sm Intest | 20.08113704 |
| Spleen | 37.91423521 |
| Stomach | 13.03461776 |
| Testis | 32.34441495 |
| Thymus | 43.05318645 |
| Thyroid | 295.3447804 |
| Uterus | 86.62062241 |

EXAMPLE 10

Expression of Human Transmembrane Serine Protease in Normal and Cancer Tissues

RNA Extraction and cDNA Preparation

Total RNA used for Taqman quantitative analysis were either purchased (Clontech, Calif.) or extracted from tissues using TRIzol reagent (Life Technologies, Me.) according to a modified vendor protocol which utilizes the RNeasy protocol (Qiagen, Calif.) Fifty µg of each RNA were treated with DNase I using RNase free-DNase (Qiagen, Calif.) for use with RNeasy or QiaAmp columns.

After elution and quantitation with Ribogreen (Molecular Probes Inc., Oreg.) each sample was reverse transcribed using the GibcoBRL Superscript II First Strand Synthesis System for RT-PCR according to vendor protocol (Life Technologies, Md.). The final concentration of RNA in the reaction mix was 50 ng/µL. Reverse transcription was performed with 0.5 µg of Oligo dT primer.

TaqMan Quantitative Analysis

Specific primers and probe were designed according to PE Applied Biosystems recommendations and are listed below:

```
forward primer: 5'-(CTGCCAGCAGCTGGGTTTC)-3'                       (SEQ ID NO:9)

reverse primer: 5'-(AGGCTTTCCTGGATGGTGGA)-3'                      (SEQ ID NO:10)

probe: 5'-(FAM)-(CAACCTCGGTTGTCCGGTGAGCACTCT)(TAMRA)-3'           (SEQ ID NO:13)
``` where FAM=6-carboxy-fluorescein
and TAMRA=6-carboxy-tetramethyl-rhodamine.
The expected length of the PCR product was-111 bp.

Quantitation experiments were performed on 25 ng of reverse transcribed RNA from each sample. Each determination was done in duplicate. 18S ribosomal RNA was measured as a control using the Pre-Developed TaqMan Assay Reagents (PDAR)(PE Applied Biosystems, Calif.). Assay reaction mix was as follows:

| | final |
|---|---|
| TaqMan Universal PCR Master Mix (2 x) (PE Applied Biosystems, CA) | 1 x |
| PDAR control - 18S RNA (20 x) | 1 x |
| Forward primer | 300 nM |
| Reverse primer | 300 nM |
| Probe | 200 nM |
| cDNA | 25 ng |
| Water to 25 uL | |
| PCR conditions: | |
| Once: | 2' minutes at 50° C. |
| | 10 minutes at 95° C. |
| 40 cycles: | 15 sec. at 95° C. |
| | 1 minute at 60° C. |

Figure 7:
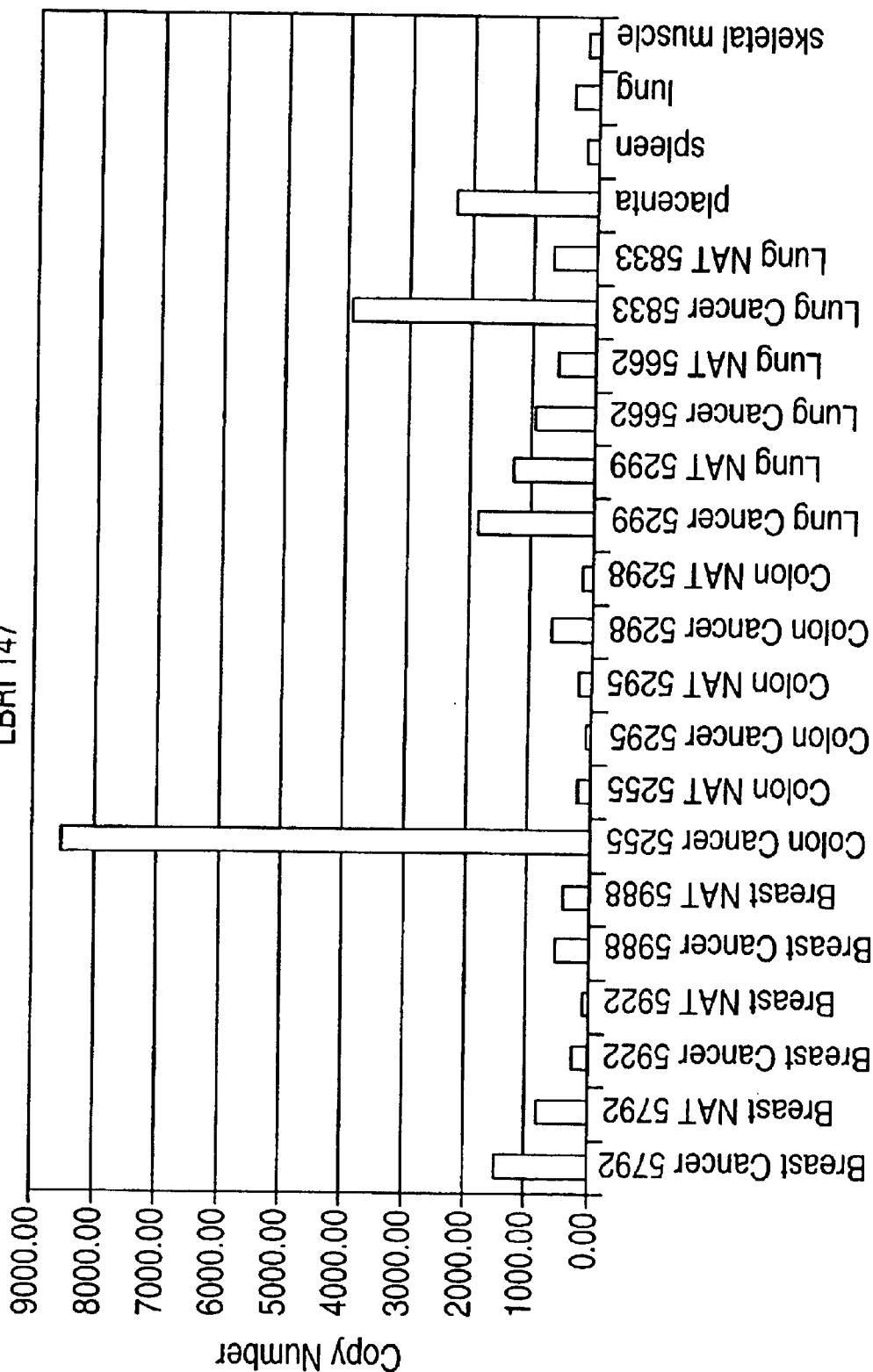
FIG. 7. Relative expression of human transmembrane serine protease in various tissues.
Figure 8:
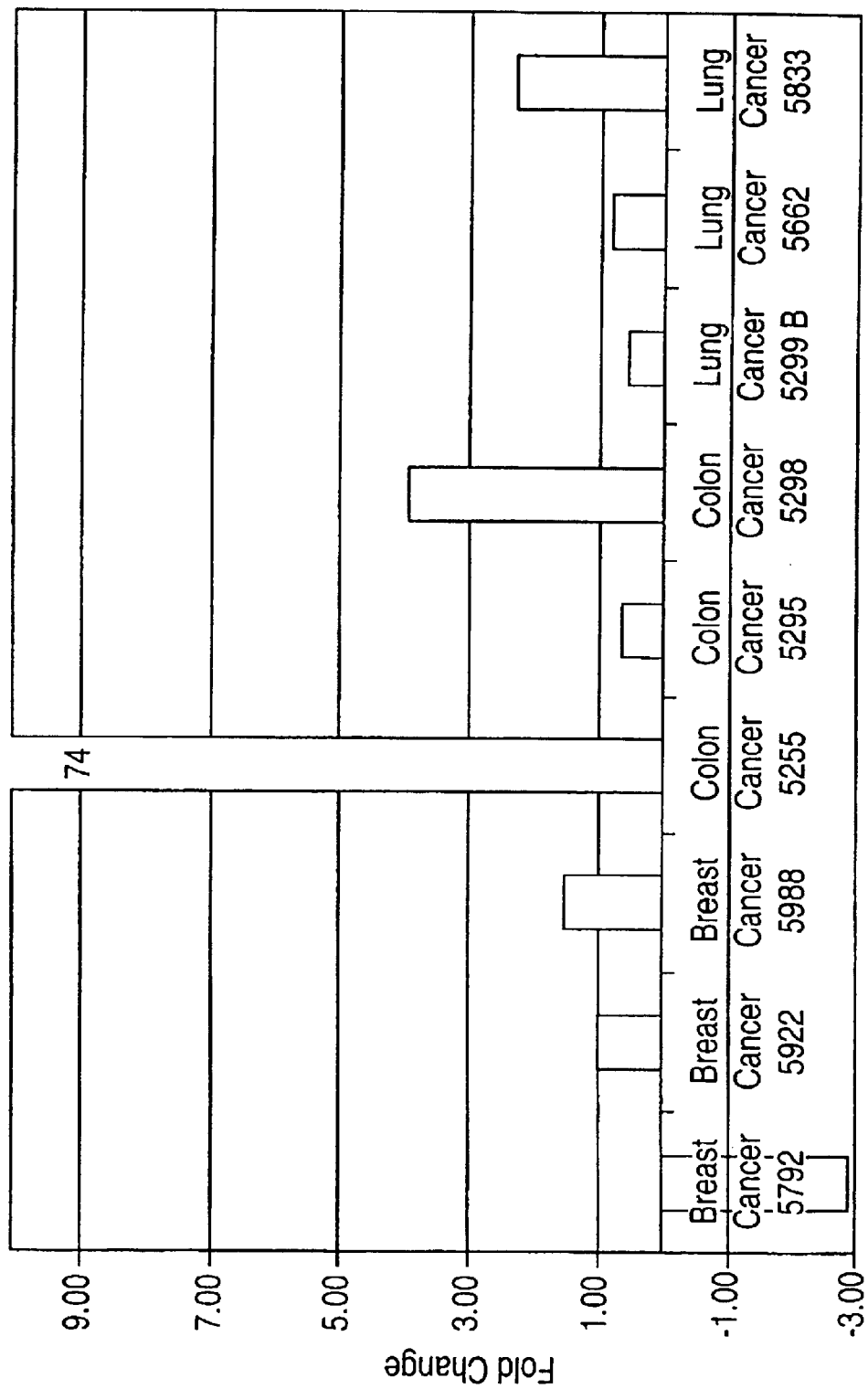
FIG. 8. Fold change in expression of human transmembrane serine protease in various cancer cells.

The experiment was performed on an ABI Prism 7700 Sequence Detector (PE Applied Biosystems, Calif.). At the end of the run, fluorescence data acquired during PCR were processed as described in the ABI Prism 7700 user's manual. Fold change was calculated using the delta—delta CT method with normalization to the 18 S values and copy number conversion was performed without normalization using the formula $Cn=10^{(ct-40.007)/-3.3623}$. The results are shown in FIGS. 7 and 8.

EXAMPLE 11

Northern Analysis

Figure 6:
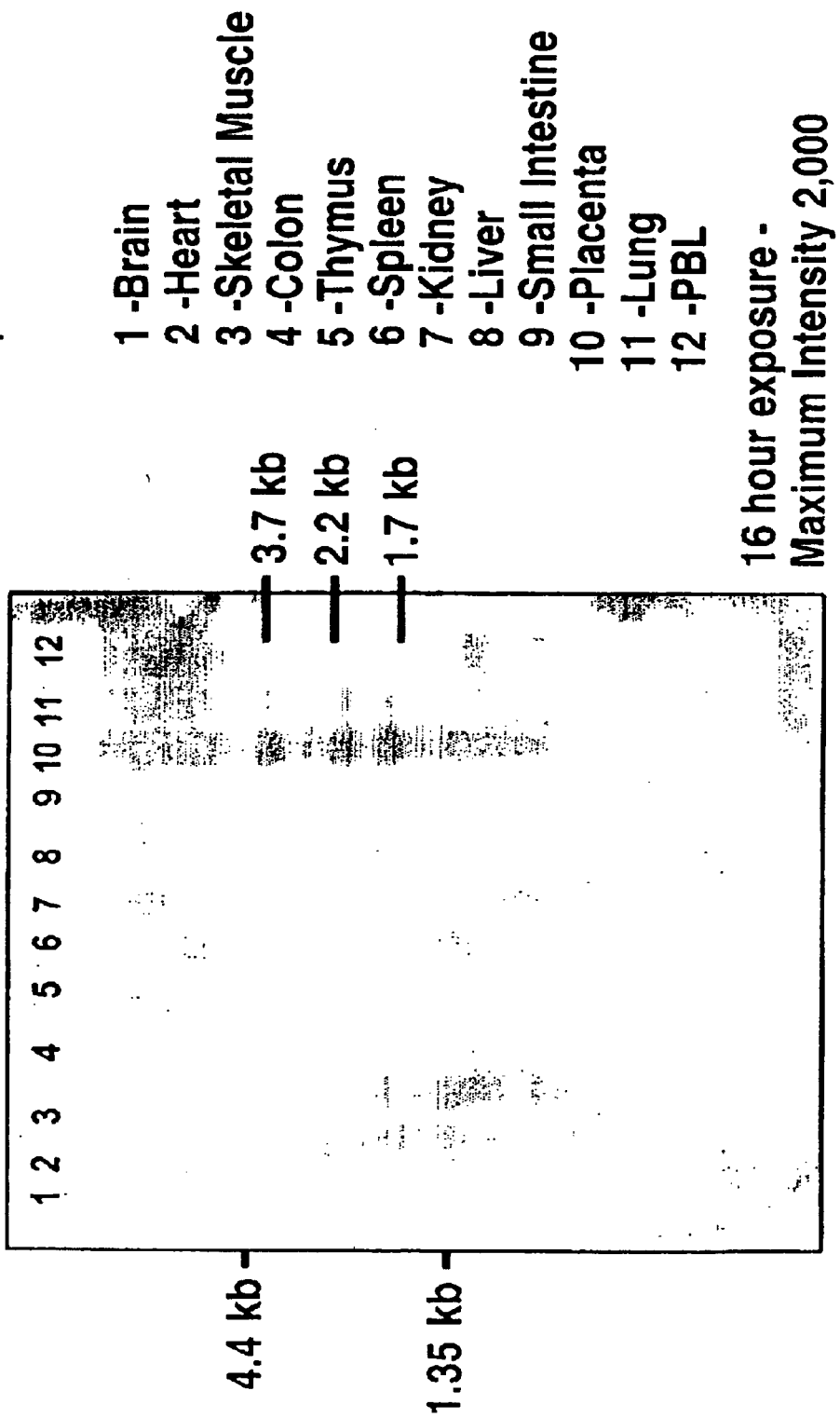
FIG. 6. Northern blot showing expression of human transmembrane serine protease.

Northern analysis was done using a human 12-lane MTN purchased from Clontech (CA). The entire coding sequence of transmembrane serine protease was used as a probe and labeled with $^{32}p$ using the Rediprime II labelling system (Amersham Pharmacia Biotech, N.J.). Hybridization and washing conditions were performed according to the Northern Max kit from Ambion (Tex.). The blot was exposed for 16 hours and the Storm 860 phosphoimager (Amersham Pharmacia Biotech, N.J.) was used to visualize the Northern analysis. The results are shown in FIG. 6.

EXAMPLE 12

Cloning of Full-Length Human Transmembrane Serine Protease

The human EST sequence having accession number BE732381 (SEQ ID NO:128) was found to overlap with the 5' end of the sequence shown in SEQ ID NO:35. BE732381 was used to search the public databases for overlapping EST and genomic sequences. No human ESTs or genomic sequences were found to extend the 5' end of that sequence. However, 5 overlapping mouse EST sequences were identified that were 80–90% identical to the sequence shown in SEQ ID NO:35 at the nucleotide level. The accession numbers for these EST sequences are: BE285038 (SEQ ID NO:127), BE289529 (SEQ ID NO:128), BE290038 (SEQ ID NO 29), BE309103 (SEQ ID NO:30), and BE286322 SEQ ID NO:31). Four of the mouse EST sequences overlapped with the 5' end of SEQ ID NO:35 and significantly extended the sequence. Translation of these ESTs revealed a putative transmembrane domain, indicating that this protein is a transmembrane serine protease.

One of the mouse ESTs, BE289529, was then selected to search the human genomic and EST databases. No significantly overlapping human EST sequences were identified. However, BE289529 aligned with a human genomic entry, AP000757. AP000757 is an unordered genomic entry for human chromosome 11. The AP000757 exon significantly extended the predicted sequence of human transmembrane protease but did not appear to encode an appropriate translational start codon. The AP000757 exon was then used to search the public databases for overlapping EST sequences.

A single human EST, BE280394 (SEQ ID NO:34), was identified that further extended the sequence at the 5' end. BE280394 was found to contain an in-frame translational start codon. This putative start codon and its flanking sequences resemble the Kozak consensus translational start sequence, suggesting that this is the translational start site for the transmembrane serine protease protein. Oligonucleotide primers flanking the predicted coding sequence were then designed to confirm that the predicted full length sequence was expressed.

PCR products of the appropriate size were identified in cDNA pools generated from placenta and spleen poly A+RNA (Clontech), confirming expression of the predicted full length cDNA. The PCR products were cloned into the pCRII vector (Invitrogen) and sequenced. The nucleotide and amino acid sequences are shown in SEQ ID NOS:11 and 12, respectively.

One of the clones isolated was a putative splice variant that lacked a region that encodes the putative transmembrane domain.

Figure 9:
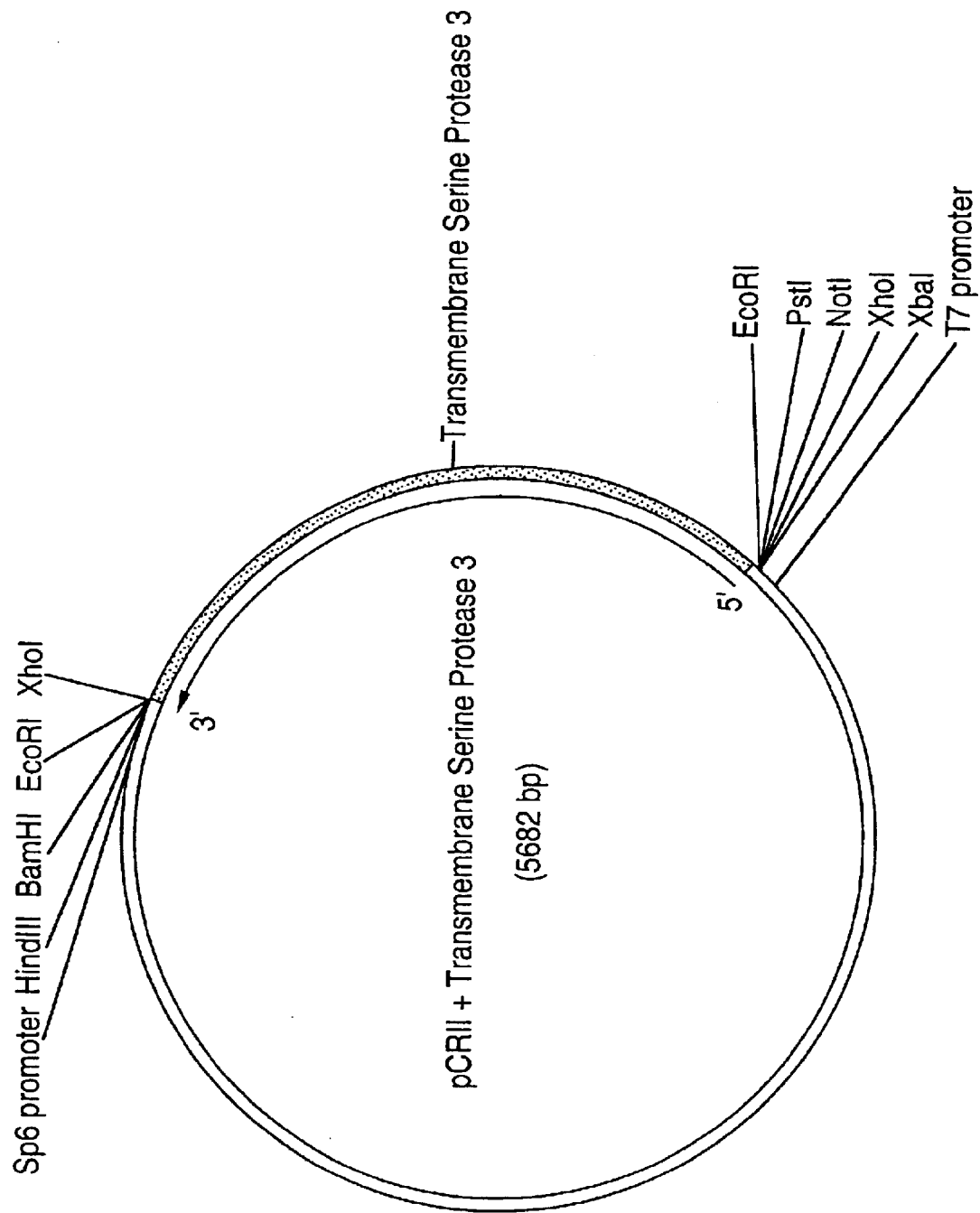
FIG. 9. Restriction map of pCRII-TMSP3.

A plasmid containing a cDNA encoding the human transmembrane serine protease, pCRII-TMSP3, was deposited under the provisions of the Budapest Treaty with the American Type Culture Collection, 10801 University Boulevard, Manassas, Va. 20110-2209 on Jun. 5, 2001, and assigned Accession No. PTA-3433. A restriction map of the deposited plasmid is shown in FIG. 9.

REFERENCES

1. Nicolson (1988) Organ specificity of tumor metastasis: Role of preferential adhesion, invasion and growth of malignant cells at specific secondary sites. *Cancer Met. Rev.* 7, 143–188.

2. Liotta et al. (1983) Tumor invasion and the extracellular matrix. *Lab. Invest.* 49, 639–649.

3. Vlodavsky et al. (1987) Endothelial cell-derived basic fibroblast growth factor: Synthesis and deposition into subendothelial extracellular matrix. *Proc. Natl. Acad. Sci. USA* 84, 2292–2296.

4. Folkman et al. (1980) A heparin-binding angiogenic protein—basic fibroblast growth factor—is stored within basement membrane. *Am. J. Pathol.* 130, 393400.

5. Cardon-Cardo et al. (1990) Expression of basic fibroblast growth factor in normal human tissues. *Lab. Invest.* 63, 832–840.

6. Vlodavsky et al. (1991) Extracellular sequestration and release of fibroblast growth factor: a regulatory mechanism? *Trends Biochem. Sci.* 16, 268–271.

7. Vlodavsky et al. (1993) Extracellular matrix-bound growth factors, enzymes and plasma proteins. In BASEMENT MEMBRANES: CELLULAR AND MOLECULAR ASPECTS Rohrbach & Timpl, eds., pp327–343. Academic Press Inc., Orlando, Fla.

8. Ross (1993) The pathogenesis of atherosclerosis: a perspective for the 1990s. *Nature (Lond.).* 362, 801–809.

9. McCarthy et al. (1986). Human fibronectin contains distinct adhesion- and motility-promoting domains for metastatic melanoma cells. *J. Cell Biol.* 102, 179-88.

10. Van Muijen et al. (1995) Properties of metastasizing and non-metastasizing human melanoma cells. *Recent Results in Cancer Research* 139, 104-22.

11. Price et al. (1997) The Biochemistry of Cancer Dissemination, in *Critical Reviews in Biochemistry and Mol. BioL* 32, 175–253.

12. Leytus et al. A novel trypsin-like serine protease (hepsin) with a putative transmembrane domain expressed by human liver and hepatoma cells. Biochemistry. 1988 Feb 9;27(3):1067–74.

13. Tanimoto et al. Hepsin, a cell surface serine protease identified in hepatoma cells, is overexpressed in ovarian cancer. Cancer Res. 1997 Jul 15;57(14):2884–7.

14. Zacharski et al., Expression of the factor VII activating protease, hepsin, in situ in renal cell carcinoma. Thromb Haemost. April 1998; 79(4):876-7.

What is claimed is:

1. A cDNA encoding a polypeptide comprising an amino acid sequence selected from the group consisting of (a) the amino acid sequence shown in SEQ ID NO:12 and (b) the ammo acid sequence encoded by a cDNA insert contained within plasmid pCRII-TMSP3 (ATCC Accession No. PTA-3433).

2. The cDNA of claim 1 which comprises the nucleotide sequence shown in SEQ ID NO:11.

3. The cDNA of claim 1 which consists of the nucleotide sequence shown in SEQ ID NO:11.

4. The cDNA of claim 1 which comprises the cDNA insert of plasmid pCRII-TMSP3.

5. The cDNA of claim 1 which consists of the cDNA insert of plasmid pCRII-TMSP3.

6. An expression vector comprising a polynucleotide which encodes a polypeptide comprising an amino acid sequence selected from the group consisting of (a) the amino acid sequence shown in SEQ ID NO:12 and (b) the amino acid sequence encoded by a cDNA insert contained within plasmid pCRII-TMSP3 (ATCC Accession No. PTA-3433).

7. The expression vector of claim 6 wherein the polynucleotide comprises the nucleotide sequence shown in SEQ ID NO:11.

8. The expression vector of claim 6 wherein the polynucleotide consists of the nucleotide sequence shown in SEQ ID NO:11.

9. The expression vector of claim 6 wherein the polynucleotide comprises the coding sequence of the cDNA insert of plasmid pCRII-TMSP3.

10. The expression vector of claim 6 wherein the polynucleotide consists of the coding sequence of the cDNA insert of plasmid pCRII-TMSP3.

11. A host cell comprising an expression vector which encodes a polypeptide comprising an amino acid sequence selected from the group consisting of (a) the amino acid sequence shown in SEQ ID NO:12 and (b) the amino acid sequence encoded by a cDNA insert contained within plasmid pCRII-TMSP3 (ATCC Accession No. PTA-3433).

12. The host cell of claim 11 wherein the polynucleotide comprises the nucleotide sequence shown in SEQ ID NO:11.

13. The host cell of claim 11 wherein the polynucleotide consists of the nucleotide sequence shown in SEQ ID NO:11.

14. The host cell of claim 11 wherein the polynucleotide comprises the nucleotide coding sequence of the cDNA insert of plasmid pCRII-TMSP3.

15. The host cell of claim 11 wherein the polynucleotide consists of the nucleotide coding sequence of the cDNA insert of plasmid pCRII-TMSP3.

16. A method of producing a polypeptide comprising an amino acid sequence selected from the group consisting of (a) the amino acid sequence shown in SEQ ID NO:12 and (b) the amino acid sequence encoded by a cDNA insert contained within plasmid pCRII-TMSP3 (ATCC Accession No. PTA-3433), comprising the steps of:

culturing a host cell comprising an expression vector that encodes the polypeptide under conditions whereby the polypeptide is expressed; and isolating the polypeptide.

17. The method of claim 16 wherein the expression vector comprises the nucleotide sequence shown in SEQ ID NO:11.

18. The method of claim 16 wherein the expression vector comprises the coding sequence of the cDNA insert of plasmid pCRII-TMSP3.

19. An isolated polynucleotide selected from the group consisting of: (a) a polynucleotide encoding a protein that comprises the amino acid sequence of SEQ ID NO:12, (b) a polynucleotide comprising the sequence of SEQ ID NO:11, (c) a polynucleotide comprising the coding sequence of a cDNA contained within plasmid pCRII-TMSP3 (ATCC Accession No. PTA-3433), and (d) a polynucleotide encoding a protein that comprises the amino acid sequence encoded by the cDNA of plasmid pCRII-TMSP3.

20. An expression vector comprising the polynucleotide of claim 19.

21. A host cell comprising the expression vector of claim 20.

22. A polynucleotide probe consisting of at least 300 contiguous nucleotides of the complete complement of a polynucleotide having the nucleotide sequence shown in SEQ ID NO:11.

23. A polynucleotide probe consisting of at least 300 contiguous nucleotides of the complete complement of a polynucleotide having the nucleotide sequence of the cDNA insert of plasmid pCRII-TMSP3 (ATCC Accession No. PTA-3433).

* * * * *